(12) United States Patent
Chigaev et al.

(10) Patent No.: US 8,911,952 B2
(45) Date of Patent: Dec. 16, 2014

(54) METHOD FOR INTEGRIN LIGAND DISCOVERY

(75) Inventors: Alexandre Chigaev, Santa Fe, NM (US); Larry A. Sklar, Albuquerque, NM (US)

(73) Assignee: STC. UNM, Albuquerque, NM (US)

( * ) Notice: Subject to any disclaimer, the term of this patent is extended or adjusted under 35 U.S.C. 154(b) by 0 days.

(21) Appl. No.: 13/583,068

(22) PCT Filed: Mar. 23, 2011

(86) PCT No.: PCT/US2011/029627
§ 371 (c)(1),
(2), (4) Date: Sep. 6, 2012

(87) PCT Pub. No.: WO2011/119732
PCT Pub. Date: Sep. 29, 2011

(65) Prior Publication Data
US 2013/0005782 A1    Jan. 3, 2013

Related U.S. Application Data

(60) Provisional application No. 61/316,913, filed on Mar. 24, 2010, provisional application No. 61/398,830, filed on Jul. 1, 2010.

(51) Int. Cl.
| | |
|---|---|
| *G01N 33/53* | (2006.01) |
| *G01N 33/68* | (2006.01) |
| *A61K 31/36* | (2006.01) |
| *A61K 31/42* | (2006.01) |
| *A61K 31/195* | (2006.01) |

(52) U.S. Cl.
CPC ............... *G01N 33/68* (2013.01); *A61K 31/36* (2013.01); *A61K 31/42* (2013.01); *G01N 2333/70546* (2013.01); *A61K 31/195* (2013.01)
USPC .......... 435/7.1; 435/7.21; 435/7.24; 435/7.95

(58) Field of Classification Search
None
See application file for complete search history.

(56) References Cited

U.S. PATENT DOCUMENTS

| | | |
|---|---|---|
| 5,306,620 A | 4/1994 | Ginsberg et al. |
| 2007/0128190 A1 | 6/2007 | Lazarides et al. |
| 2007/0249061 A1 | 10/2007 | Han et al. |
| 2008/0286269 A1 | 11/2008 | Violette et al. |

OTHER PUBLICATIONS

Van Regenmortel MHV. Mapping Epitope Structure and Activity: From One-Dimensional Prediction to Four-Dimensional Description of Antigenic Specificity Methods. 9(3):465-72, 1996.*

Ahrens and Peter. Therapeutic integrin inhibition: Allosteric and activation-specific inhibition strategies may surpass the initial ligand-mimetic strategies. Thromb Haemost 2008; 99:803-804.*
Chen, Wei. The force regulation on binding kinetics and conformations of integrin and selectins using a bio-membrane force probe. Dissertation Abstracts International, (2009) vol. 71, No. 7B, p. 4377. Order No. AAI3414684. 166 pages.*
Woods et al. Activation-dependent changes in soluble fibronectin binding and expression of β1 integrin activation epitopes in T cells: relationship to T cell adhesion and migration. Eur. J. Immunol. 2000. 30: 38-49.*
Welzenbach et al., Small Molecule Inhibitors Induce Conformational Changes in the IDomain and the I-like Domain of Lymphocyte Function-associated Antigen-1. Molecular Insights Into Integrin Inhibition. J. Biol. Chem. 2002, 277:10590-10598.*
Lapidot, T. and Petit, I. (2002) Exp.Hematol. 30, 973-981.
Lapidot, T., Dar, A., and Kollet, O. (2005) Blood 106, 1901-1910.
Johnson, J. P. (1999) Cancer Metastasis Rev. 18, 345-357.
Yoneda, T. (2000) J.Orthop.Sci. 5, 75-81.
Yusuf-Makagiansar, H., Anderson, M. E., Yakovleva, T. V., Murray, J. S., and Siahaan, T. J. (2002) Med.Res.Rev. 22, 146-167.
Jackson, D. Y. (2002) Curr.Pharm.Des 8, 1229-1253.
Schmidmaier, R. and Baumann, P. (2008) Curr.Med.Chem. 15, 978-990.
Dijkgraaf, I., Beer, A. J., and Wester, H. J. (2009) Front Biosci. 14, 887-899.
Humphries, M. J. (2004) Biochem.Soc.Trans. 32, 407-411.
Shimaoka, M. and Springer, T. A. (2003) Nat.Rev.Drug Discov. 2, 703-716.
Woodside, D. G. and Vanderslice, P. (2008) BioDrugs. 22, 85-100.
Frelinger, A. L., III, Du, X. P., Plow, E. F., and Ginsberg, M. H. (1991) J.Biol.Chem. 266, 17106-17111.
Frelinger, A. L., III, Cohen, I., Plow, E. F., Smith, M. A., Roberts, J., Lam, S. C., and Ginsberg, M. H. (1990) J.Biol. Chem. 265, 6346-6352.
Mould, A. P., Barton, S. J., Askari, J. A., McEwan, P. A., Buckley, P. A., Craig, S. E., and Humphries, M. J. (2003) J. Biol.Chem. 278, 17028-17035.
Chigaev, A., Waller, A., Amit, O., Halip, L., Bologa, C. G., and Sklar, L. A. (2009) J.Biol.Chem. 284, 14337-14346.
Njus, B. H., Chigaev, A., Waller, A., Wlodek, D., Ostopovici-Halip, L., Ursu, O., Wang, W., Oprea, T. I., Bologa, C. G., and Sklar, L. A. (2009) Assay.Drug Dev.Technol. 7, 507-515.
Sudeshna, G. and Parimal, K. (2010) Eur.J.Pharmacol. 648, 6-14.
Shen, W. W. (1999) Compr.Psychiatry 40, 407-414.
Thanacoody, H. K. (2007) Br.J.Clin.Pharmacol. 64, 566-574.
Roudebush, R. E., Berry, P. L., Layman, N. K., Butler, L. D., and Bryant, H. U. (1991) Int.J.Immunopharmacol. 13, 961-968.
Surman, O. S. (1993) Psychosomatics 34, 139-143.
Chigaev, A., Blenc, A. M., Braaten, J. V., Kumaraswamy, N., Kepley, C. L., Andrews, R. P., Oliver, J. M., Edwards, B. S., Prossnitz, E. R., Larson, R. S., and Sklar, L. A. (2001) J.Biol.Chem. 276, 48670-48678.

(Continued)

*Primary Examiner* — Maher Haddad
(74) *Attorney, Agent, or Firm* — Henry D. Coleman; R. Neil Sudol

(57) ABSTRACT

This invention relates generally to integrin ligand discovery and to a method of integrin ligand discovery base upon induction of ligand-induced epitopes. Such ligands have the potential to be active agent as anti-inflammatory, anti-angiogenesis and/or anti-thrombotic agents and for the treatment of integrin mediated diseases and/or conditions.

41 Claims, 14 Drawing Sheets

(56) References Cited

OTHER PUBLICATIONS

Chigaev, A., Zwartz, G., Graves, S. W., Dwyer, D. C., Tsuji, H., Foutz, T. D., Edwards, B. S., Prossnitz, E. R., Larson, R. S., and Sklar, L. A. (2003) J.Biol.Chem. 278, 38174-38182.

Chigaev, A., Buranda, T., Dwyer, D. C., Prossnitz, E. R., and Sklar, L. A. (2003) Biophys.J. 85, 3951-3962.

Osborn, L., Hession, C., Tizard, R., Vassallo, C., Luhowskyj, S., Chi-Rosso, G., and Lobb, R. (1989) Cell 59, 1203-1211.

Sklar, L. A., Edwards, B. S., Graves, S. W., Nolan, J. P., and Prossnitz, E. R. (2002) Annu.Rev.Biophys.Biomol.Struct. 31, 97-119.

Zwartz, G., Chigaev, A., Foutz, T., Larson, R. S., Posner, R., and Sklar, L. A. (2004) Biophys.J. 86, 1243-1252.

Edwards, B. S., Curry, M. S., Tsuji, H., Brown, D., Larson, R. S., and Sklar, L. A. (2000) J.Immunol. 165, 404-410.

Chigaev, A., Waller, A., Zwartz, G. J., Buranda, T., and Sklar, L. A. (2007) J.Immunol. 178, 6828-6839.

Chigaev, A., Waller, A., Amit, O., and Sklar, L. A. (2008) BMC. Immunol. 9, 26.

Gazitt, Y. (2004) Leukemia 18, 1-10.

Oostendorp, R. A. and Dormer, P. (1997) Leuk.Lymphoma 24, 423-435.

Coulombel, L., Auffray, I., Gaugler, M. H., and Rosemblatt, M. (1997) Acta Haematol. 97, 13-21.

Bonig, H., Wundes, A., Chang, K. H., Lucas, S., and Papayannopoulou, T. (2008) Blood 111, 3439-3441.

Zohren, F., Toutzaris, D., Kiarner, V., Hartung, H. P., Kieseier, B., and Haas, R. (2008) Blood 111, 3893-3895.

Papayannopoulou, T. and Nakamoto, B. (1993) Proc.Natl.Acad.Sci. U.S.A 90, 9374-9378.

Bonig, H., Watts, K. L., Chang, K. H., Kiem, H. P., and Papayannopoulou, T. (2009) Stem Cells 27, 836-837.

Ramirez, P., Rettig, M. P., Uy, G. L., Deych, E., Holt, M. S., Ritchey, J. K., and DiPersio, J. F. (2009) Blood 114, 1340-1343.

Broxmeyer, H. E., Orschell, C. M., Clapp, D. W., Hangoc, G., Cooper, S., Plett, P. A., Liles, W. C., Li, X., Graham-Evans, B., Campbell, T. B., Calandra, G., Bridger, G., Dale, D. C., and Srour, E. F. (2005) J.Exp.Med. 201, 1307-1318.

Hatse, S., Princen, K., Bridger, G., De Clercq, E., and Schols, D. (2002) FEBS Lett. 527, 255-262.

Liles, W. C., Broxmeyer, H. E., Rodger, E., Wood, B., Hubei, K., Cooper, S., Hangoc, G., Bridger, G. J., Henson, G. W., Calandra, G., and Dale, D. C. (2003) Blood 102, 2728-2730.

Hendrix, C. W., Flexner, C., MacFarland, R. T., Giandomenico, C., Fuchs, E. J., Redpath, E., Bridger, G., and Henson, G. W. (2000) Antimicrob.Agents Chemother. 44, 1667-1673.

Chedid, L. (1954) C.R.Seances Soc.Biol.Fil. 148, 1039-1043.

Trifiro, G., Gambassi, G., Sen, E. F., Caputi, A. P., Bagnardi, V., Brea, J., and Sturkenboom, M. C. (2010) Ann.Intern. Med. 152, 418-440.

Matthews, N., Franklin, R. J., and Kendrick, D. A. (1995) Biochem. Pharmacol. 50, 1053-1061.

Pollmacher, T., Haack, M., Schuld, A., Kraus, T.; and Hinze-Selch, D. (2000) J.Psychiatr.Res. 34, 369-382.

Berger, J. R. and Houff, S. (2006) Neurol.Res. 28, 299-305.

Rigal, E., Gateault, P., Lebranchu, Y., and Hoarau, C. (2009) Med. Sci.(Paris) 25, 1135-1140.

Fieve, R. R., Blumenthal, B., and Little, B. (1966) Arch.Gen.Psychiatry 15, 529-534.

Kenakin, T. (2004) Mol.Interv. 4, 222-229.

Arnaout, M. A., Mahalingam, B., and Xiong, J. P. (2005) Annu.Rev. Cell Dev.Biol. 21, 381-410.

Tang, R. H., Tng, E., Law, S. K., and Tan, S. M. (2005) J.Biol.Chem. 280, 29208-29216.

Shimaoka M et al.; Therapeutic Antagonists and Conformational Regulation of Integrin Function;Nature Reviews Drug Discovery 2003; 2:703-716.

Njus, B. et al.; Conformational mAb as a Tool for Integrin Ligand Discovery. Assay and Drug Development Technologies Oct. 2009; vol. 7, No. 5.

\* cited by examiner

MLS000085920

MLS000044001

MLS000085916

MLS000521558

MLS000521553

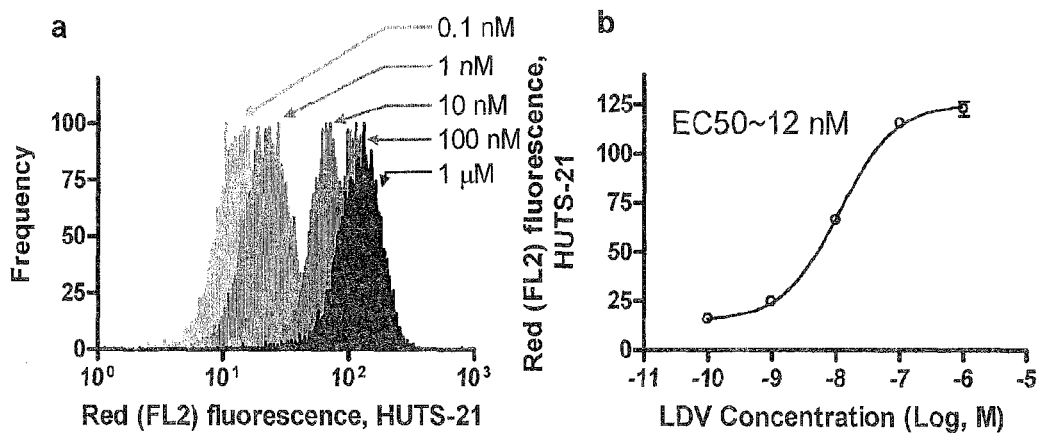
FIG. 3
Figure 4
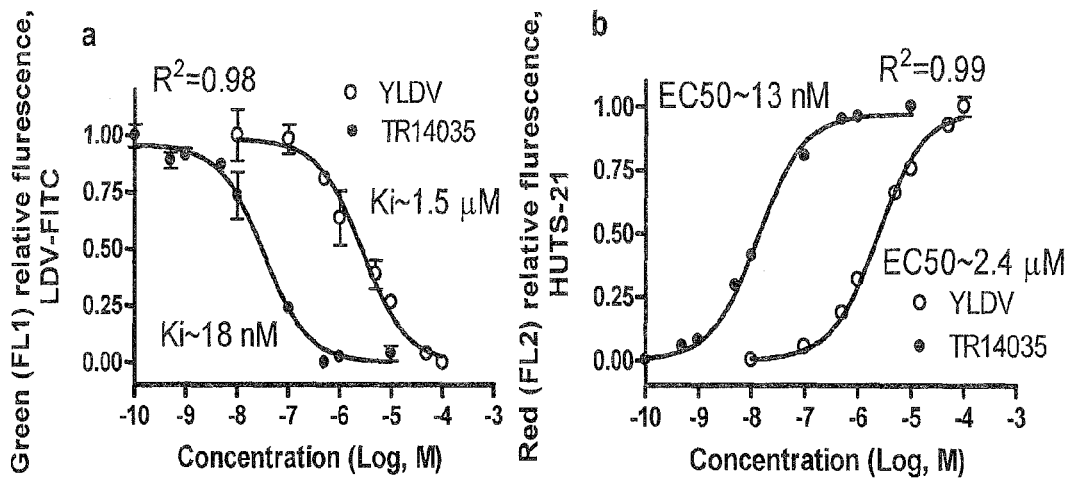
FIG. 4

Compound 3
Genentech

XVA143
Roche

FIG. 12A and B
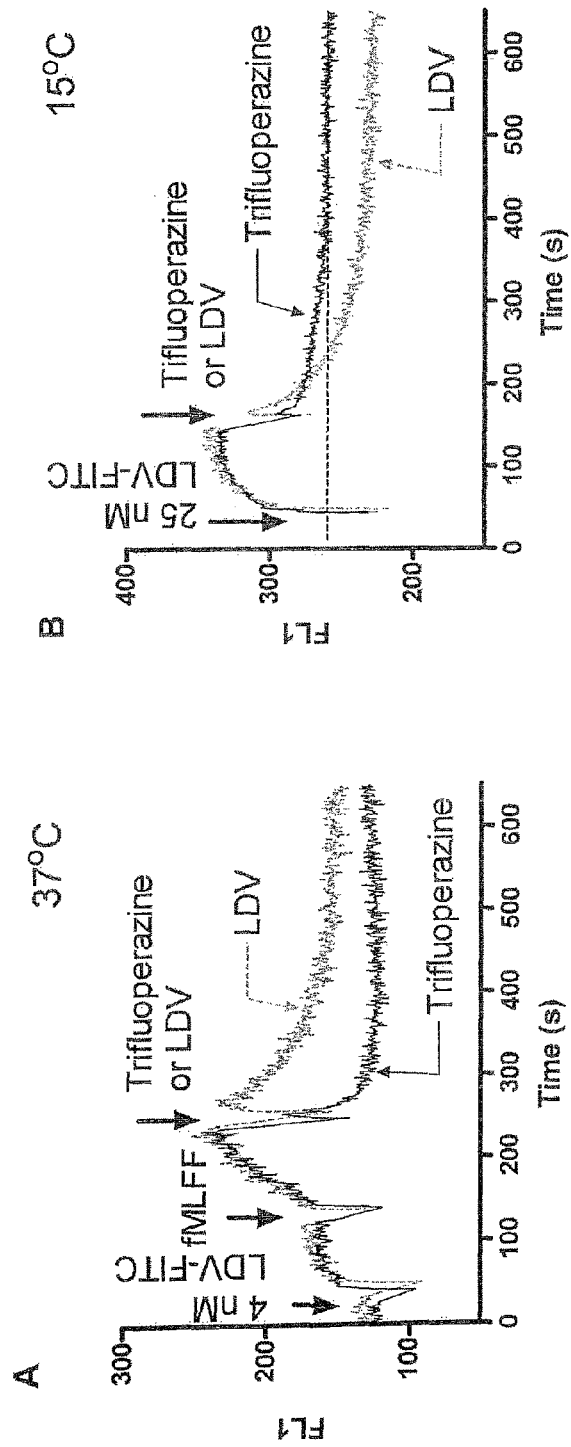

METHOD FOR INTEGRIN LIGAND DISCOVERY

RELATED APPLICATIONS AND GRANT SUPPORT

This application is a United States national phase application of and claims the benefit of priority of International Patent Application No. PCT/US2011/029627 filed Mar. 23, 2011 of identical title, said application claims the benefit of priority of U.S. provisional application No. 61/316,913, filed Mar. 24, 2010 of identical title to the present application and U.S. 61/398,830, filed Jul. 1, 2010, also of identical title to the present application, all three applications being incorporated by reference in their entirety herein.

This patent application was supported by Grant No. R01 HL081062 awarded by the National Institutes of Health. The Government has certain rights in the invention.

FIELD OF THE INVENTION

This invention relates generally to integrin ligand discovery and, more specifically, to a method of integrin ligand discovery based upon induction of ligand-induced epitopes. The present invention also relates to compounds that have been identified as integrin ligands (as modulators of integrin such as agonists and antagonists) and their role as therapeutic agents for treating disease states and/or conditions which are mediated through integrin receptors. Methods of treating diseases that are mediated through integrin receptors represent another part of the present invention.

BACKGROUND OF THE INVENTION

Integrins are cell surface receptors that mediate cell to cell, or cell to extracellular matrix adhesion. They play a major role in the regulation of immune cell recruitment to inflamed endothelia and sites of inflammation. Integrins participate in antigen presenting cell-lymphocyte interactions, retention and mobilization of immature progenitors in the bone marrow, cancer cell trafficking, metastasis and other events. They represent a target for several existing drugs for treatment of inflammatory diseases, anti-angiogenic therapy, and anti-thrombotic therapy, among others. Integrin ligands can also be used as imaging tools. Integrin dependent adhesion avidity is regulated by a number of conformational changes of the protein. These can occur without a significant change in the expression levels of the molecules. Conformational changes include an increase in the affinity of the ligand binding pocket, and others, that consists of the unbending (extension) of the integrin, along with hybrid domain swing, as well as integrin "leg" separation. Recent data suggest that at least some of these conformations are regulated independently from the others. Conformational changes can be detected using conformationally sensitive antibodies, which bind to defined epitopes exposed only in certain molecular conformations. Some of these are known to be induced by the binding of the ligand (so called ligand induced binding sites (LIBS)). Several antibody epitopes have been mapped to the part of the VLA-4 integrin surface between α and β1-subunits, which is hidden in the resting, low affinity state because of the close subunit proximity, and exposed upon activation and/or ligand binding. The integrin conformation with exposed epitopes is attributed to the high affinity activation state in one model of integrin activation and the ligand occupied conformation according to another. However, despite differing opinions about the role of epitope exposure, epitope exposure represents a valuable tool for monitoring integrin conformations using flow cytometery techniques.

Discovery of new small molecules that bind to the integrin ligand binding site and block interaction with its natural ligand, is part of the ongoing drug discovery process. The ability to detect specific binding of the ligand and determine its binding affinity is critical for these approaches. In this case a desirable assay would be if the binding of the unlabeled small molecule could be detected in a homogeneous assay. Here we describe a novel approach for the detection of the ligand binding affinity based upon induction of ligand induced epitopes. Using commercially available conformationally sensitive mAbs we were able to confirm induction of ligand induced epitopes, as well as ligand binding affinity for two previously described VLA-4 integrin ligands. $EC_{50}$ values for the conformational mAb binding showed a good correlation with $K_i$s determined in the competitive binding assay with a well characterized fluorescent ligand. We have also determined binding constants for two novel VLA-4 ligands, and verified them using a competitive binding assay. Ligands which induce activation epitopes may formally be referred to as agonists if they also induce intracellular signaling. This current approach can be extended to other integrins, and can be adapted for a high-throughput flow cytometry format.

From a therapeutic point of view integrins are the most important class of cell adhesion receptors that mediate cell to cell, or cell to extracellular matrix adhesion. VLA-4 (very late antigen 4, $\alpha_4\beta_1$-integrin, CD49d/CD29) plays a major role in the regulation of immune cell recruitment to inflamed endothelia and sites of inflammation. It participates in antigen presenting cell-lymphocyte interactions, retention and mobilization of immature progenitors in the bone marrow, cancer cell trafficking, metastasis and other events. Integrins represent an attractive target for several existing drugs for treatment of inflammatory diseases, anti-angiogenic therapy, and anti-thrombotic therapy, among others as described herein. Integrin ligands can also be used as imaging tools, as well as probes for studies of integrin functional activity and molecular conformation.

Multiple small molecules have been developed in an attempt to regulate integrin dependent adhesion. Competitive antagonists can bind to the natural ligand binding pocket, and block interaction between integrins and integrin natural ligands. Because the binding pocket is located between the α subunit and β subunit I-like domain they also are termed α/β I-like competitive antagonists. Multiple compounds of this type were developed for $\alpha_{IIb}\beta_3$, $\alpha_v\beta_3$, and $\alpha_4\beta_1$ integrins. Several integrins have an additional domain that is inserted within α-subunit β-propeller (A domain or I domain), which is evolutionarily related to the β I-like domain. The I domain serves as a ligand binding site for these integrins. Two types of allosteric antagonists for these integrins have been described: α/β I-like allosteric antagonists and α I allosteric antagonists. Previously, no allosteric antagonists have been identified for non I domain containing integrins (such as VLA-4). Using the method described in the invention we were first to identify VLA-4 integrin allosteric antagonists (Chigaev, et al., *J Biol Chem.* 286, 5455-63 (2011)).

One of the features of integrin competitive antagonists is to occupy the ligand binding pocket and induce a conformational change that is similar to the conformational change induced by a natural ligand. Recently, the present inventors showed that this feature can be used for the identification of unknown integrin antagonists, and determination of the ligand binding affinity for unlabelled small integrin ligands, See, Njus, et al., *Assay. Drug Dev. Technol.* 7, 507-515 (2009)

and Chigaev, et al., *J. Biol. Chem.* 284, 14337-14346 (2009), Chigaev, et al., *J Biol Chem.* 286, 5455-63 (2011).

We have modified the existing assay to specifically detect only VLA-4 allosteric antagonists, and performed high-throughput flow cytometry-based screen of the Prestwick Chemical Library (PCL), which represents one of "smart screening libraries" designed to decrease a number of "low quality" hits.

In the present application, several structurally related compounds that were able to prevent exposure of ligand induced binding sites (LIBS) after the addition of VLA-4 specific ligand, decrease binding affinity of VLA-4 specific ligand, and block VLA-4/VCAM-1 dependent cell adhesion are reported. Because these compounds are previously used or currently marketed drugs, which are known to possess immunosuppressive properties that are specifically attributed to the cell mediated component (4), this effect upon VLA-4 ligand binding provides a plausible explanation for the mechanism of immunosuppression.

OBJECTS OF THE INVENTION

It is an object of the invention to provide assay methods, which may be used to identify the existence of specific integrin modulators from a collection of compounds having unknown integrin activity using integrin ligand binding induced epitopes.

It is another object of the invention to provide assay methods for identifying competitive binding ligands for integrin proteins.

It is yet an additional object of the invention to provide assay methods for identifying allosteric/non-canonical inhibitors of integrin proteins.

It is still another object of the invention to provide diagnostic and/or treatment methods for compounds which are identified as integrin modulators.

It is yet another object of the invention to provide pharmaceutical compositions based upon compounds identified as having integrin modulation activity.

Any one or more of these and/or other object of the invention may be readily gleaned as from a review of the description of the invention which follows.

BRIEF DESCRIPTION OF THE INVENTION

As described herein, the preferred embodiments of the present invention provide a method of using ligand-induced epitopes for the detection of unknown integrin ligands. The methods of the present invention are used to identify modulators (agonists, antagonists and allosteric inhibitors) of integrin which may be used as ligands for the identification of further ligands, for diagnostic applications and for therapeutic applications involving or mediated through integrins. In preferred aspects of the invention, the methods are used to identify ligands of integrins which may be used to a treat a number of disease states and/or conditions which are modulated through integrin molecules.

The present invention makes use of the fact that ligands of integrin, when they bind to integrin, will expose certain epitopes on the integrin molecule. These integrin ligand induced epitopes become targets for antibodies, which are specific for those epitopes. By providing a means of reporting the binding of an integrin epitope specific antibody (e.g. by including a fluorescent label or other reporter moiety on an anti-integrin antibody, preferably a monoclonal antibody), conformational changes in the integrin molecule which occur as a consequence of the binding of a ligand and exposure of the epitope may be identified.

Thus, in a first aspect, the present invention is directed to a method of identifying whether a compound of unknown integrin activity is a competitive ligand of an integrin molecule comprising exposing said integrin molecule (the integrin is preferably expressed on the surface of a wild-type cell which naturally expresses sufficiently quantities of the target integrin or is engineered to express the target integrin in amounts effective to be used in a cell-based assay) to a compound of unknown activity, allowing a sufficient time for said compound to bind to said integrin if said compound is a ligand of said integrin; and thereafter, exposing said integrin molecule to an integrin epitope binding antibody comprising a reporter; and determining whether the compound is a ligand of integrin by measuring the concentration of antibody bound to said integrin and comparing it to a control. In instances where significant monoclonal antibody is bound to the target integrin (above specific binding of the antibody to the target integrin), the compound is identified as a competitive ligand of integrin (agonist or antagonist). Optionally, the compound is then used in alternative integrin assays which measure agonist or antagonist integrin activity of the compound. Assays, in particular cell based assays adapted to flow cytometry, especially high throughput flow cytometry, are additional preferred aspects of the invention.

In an alternative embodiment, the present invention is directed to a method for determining whether or not a compound of unknown integrin activity is an allosteric (non-canonical) inhibitor of an integrin molecule. In this method, a cell which expresses sufficient quantities of an integrin molecule (either as a wild-type or engineered cell as described above) is exposed to a known competitive ligand (preferably an agonist) of the integrin molecule in the presence of a integrin-epitope binding antibody, preferably, a monoclonal antibody comprising a reporter moiety, and the binding of the monoclonal antibody to the ligand induced epitope in the presence of the competitive ligand is measured (which measurement may be used to establish a baseline or control); the bound integrin molecule is thereafter exposed to a compound of unknown activity and after a sufficient period to allow to the compound of unknown activity to displace the known competitive ligand from the integrin molecule, the binding of the antibody to the integrin molecule is measured, wherein the decrease in binding of antibody to integrin to a level about that of the specific binding of the antibody to the integrin molecule is evidence that the compound of unknown activity is an allosteric inhibitor of integrin. In this aspect of the invention, two controls are preferably used. The first is a control which establishes the binding of the ligand-induced epitope by the epitope binding antibody and the second is a control which establishes the specific binding of the epitope binding antibody to the integrin molecule in the absence of a competitive ligand of integrin.

In additional aspects of the invention, integrin modulators, i.e., those compounds which have been identified as competitive agonists or antagonists, or allosteric inhibitors of integrin are used in the diagnosis and treatment of an integrin-mediated disease or disorder (condition). Thus, methods of diagnosing or treating an integrin mediated disease or disorder (condition) in a patient in need thereof, are another aspect of the invention. In this method, an effective amount of one or more compounds according to the present invention are administered to a patient in need thereof to diagnose a condition or disease state or to treat or reduce the likelihood of a condition or disease state in a patient in need. Disease states or disorders (conditions) which may be diagnosed, treated or reduced in likelihood by the present invention include, for example, nervous system diseases and/or disorders including; for example, multiple sclerosis, myasthenia gravis, neuropathy, uveitis; circulatory system diseases and/or disorders including hemolytic anemia, pernicious anemia, thrombocytopenia, temporal arteritis, anti-phospholipid syndrome, Wegener's granulomatosis, Behset's disease; musculoskeletal diseases and/or disorders including rheumatoid arthritis, scleroderma, spondyloarthropathies, Sjogren's dyndrome, systemic lupus erythematosus, polymyositis dermatomyositis, ankylosing spondylitis; gastrointestinal system diseases and/or disorders including Crohn's disease, primary biliary cirrhosis, hepatitis (B and/or C), ulcerative colitis; endocrine system diseases and/or disorders including diabetes mellitus (type 1), Grave's disease, Hashimoto's thyroiditis, oophoritis; skin diseases and/or disorders including psoriasis, dermatitis herpetiformis, pemphigus vulgaris, vitiligo; and respiratory diseases and/or disorders including asthma. See, for example, Jackson, D. Y., *Curren Pharm Des,* 8:1229-1253 (2002).

The present invention also relates to compounds according to the formula I:

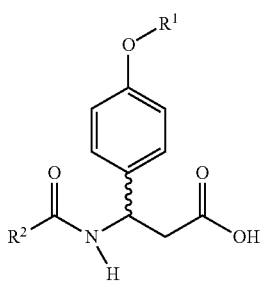

Where R¹ is $C_1$-$C_4$ linear or branched alkyl group; and R² is an optionally substituted cyclic or bicyclic hydrocarbon or an optionally substituted 5-10 membered heterocyclic ring or fused bicyclic ring system, or a pharmaceutically acceptable salt, solvate or polymorph thereof.

The compound of formulation I may also be represented by its two enantiomeric configurations as set forth below:

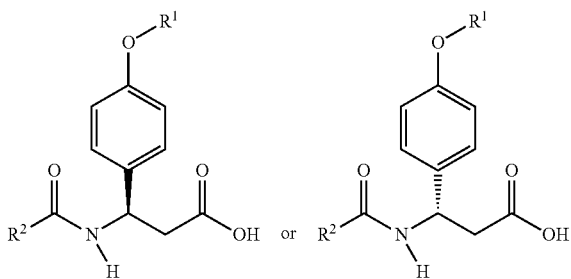

where R¹ and R² are the same as above, or a pharmaceutically acceptable salt thereof.

In preferred aspects according to the present invention, R¹ is preferably a $C_2$-$C_3$ alkyl group (i.e., ethyl, propyl, isopropyl) and R² is preferably a cyclohexyl group, a disubstituted ($C_1$-$C_3$ alkyl and phenyl substituted) isoxazole group; a benzodioxolanyl group

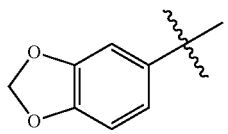

or an adamantyl group

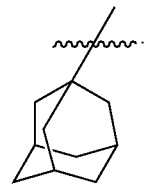 [SMILES: *C12CC3CC(CC(C3)C1)C2]

Additional particularly preferred compounds according to the present invention are those which are set forth in FIG. 1 hereof, or a pharmaceutically acceptable salt.

The present invention also relates to pharmaceutical compositions comprising an effective amount of an integrin modulator according to formula I, as set forth above, or as otherwise described herein (which may be a competitive integrin inhibitor, an integrin agonist or an allosteric inhibitor of integrin) in combination with a pharmaceutically acceptable carrier, additive and/or excipient.

Other aspects of the invention may be readily gleaned from a review of the invention which is presented herein.

BRIEF DESCRIPTION OF THE DRAWINGS

FIG. 3 shows the binding of HUTS-21 to U937 cells in the presence of different concentrations of LDV. In (a) Cells were incubated with the indicated concentration of LDV in the presence of an excess of HUTS-21 mAbs, washed, and fluorescence was measured (5000 events were collected); and (b) Mean fluorescence intensity plotted vs. concentration of LDV (data replotted from panel a).

FIG. 4 shows competition between novel VLA-4 ligands and LDV-FITC ligand, and their effect upon HUTS-21 epitope exposure. In (a) competitive binding of LDV-FITC ligand to U937 cells in the presence of different concentrations of YLDV or TR14035; and in (b) binding of HUTS-21 to cells in the presence of different concentrations of YLDV or TR14035.

DETAILED DESCRIPTION

Figure 1:
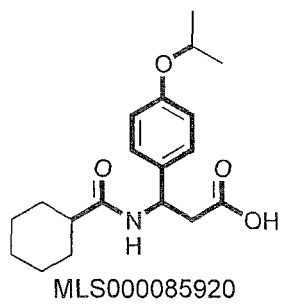
FIG. 1 shows the structure of molecules identified in screening and virtual screening, where Maximum Common Substructure (MCS) is highlighted in bold.
Figure 1:
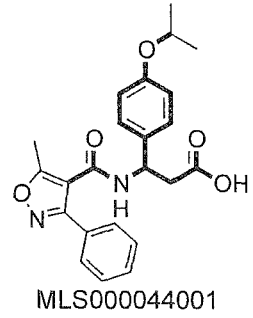
Figure 1:
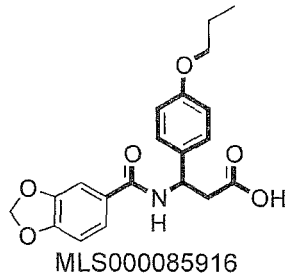
Figure 1:
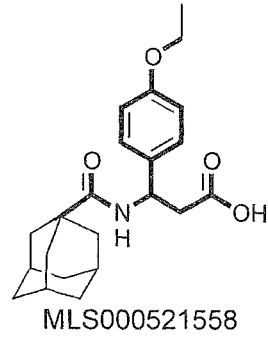
Figure 1:
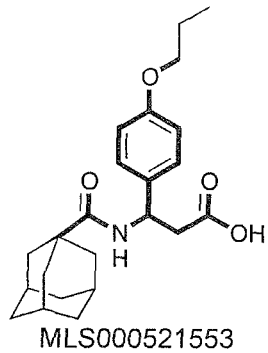

Below are the details of certain embodiments, however, this does not limit other embodiments from using other suitable methods or materials. Those of skill in the art will appreciate that the following description is related to preferred and/or example embodiments of the present invention. Certain embodiments of the present invention are defined exclusively within the appended claims.

The following definitions and terms are used throughout the specification to describe the present invention.

The term "patient" or "subject" is used throughout the specification to describe an animal, preferably a human, to whom treatment, including prophylactic treatment, with the compounds according to the present invention is provided. For treatment of those infections, conditions or disease states which are specific for a specific animal such as a human patient, the term patient refers to that specific animal.

The term "compound" is used herein to refer to any specific chemical compound disclosed herein. Within its use in context, the term generally refers to a single modulator (agonist or antagonist) as a small molecule, but in certain instances may also refer to stereoisomers and/or optical isomers (including racemic mixtures) of disclosed compounds. It is noted that when the stereochemistry about a chiral center is not specifically indicated, all stereoisomers are understood to be disclosed by the structure. In particular, a chiral center will represent both possible enantiomers about the chiral center. In certain instances, within context, the term compound may refer to a polypeptide or related molecule (as in the case of integrin, etc.)

The term "effective amount" is used throughout the specification to describe concentrations or amounts of compounds according to the present invention which may be used to produce a favorable change in a disease or condition treated, whether that change is a remission, a favorable physiological result, a reversal or attenuation of a disease state or condition treated, the prevention or the reduction in the likelihood of a condition or disease-state occurring, depending upon the disease or condition treated. Where compounds are used in combination, each of the compounds is used in an effective amount, wherein an effective amount may include a synergistic amount.

The term "integrin" is used to describe a cell surface receptor that mediates cell to cell, or alternatively, cell to extracellular adhesion molecules. Integrins are heterodimeric transmembrane receptor proteins of animal cells that bind to components of the extracellular matrix on the outside of the cell and to components on the inside of the cell, thus connecting the cell interior to its exterior. In certain cells, for example blood cells, integrins are also involved in cellular adhesions.

Integrins are conformationally flexible molecules. Integrin conformation modulates primary function of integrins: regulation of cell adhesion. Different integrin conformations result in the exposure of neoepiotpes, which can be detected using antibodies (mAbs) directed against these epitopes. Conformationally sensitive anti-integrin antibodies, termed "activation epitopes", "activation-reporter mAbs", "ligand-induced-binding site (LIBS) mAbs", and) others, are widely commercially available (Table I).

Drug-like small molecules, integrin ligands, agonists, antagonists, and other conformational modulators have a potential to specifically target, and actively perturb integrin molecular conformation. The binding of conformationally sensitive antibodies can be used as a reporter to discover novel integrin modulators. Because antibodies are integrin-specific, assays can be performed on cells expressing several different integrins. Because antibodies can be specifically labeled (for example using different fluorophores) it is possible to perform multiplex assays, where several different integrins are analyzed simultaneously. The method is expected to facilitate discovery of small molecules specifically targeting different integrins, and thus, to enhance drug-discovery efforts for treatment of numerous pathologies as otherwise described herein.

In particular, integrins play a major role in the regulation of immune cell recruitment to inflamed endothelia and sites of inflammation. Integrins participate in antigen presenting cell-lymphocyte interactions, retention and mobilization of immature progenitors in the bone marrow, cancer cell trafficking, metastasis and other events. They represent a target for several existing drugs for treatment of inflammatory diseases, anti-angiogenic therapy, and anti-thrombotic therapy, among others.

Generally, integrins contain $\alpha$ and $\beta$ subunits which are noncovalently bonded. The subunits are generally labeled $\alpha_1$ to $\alpha_8$, $\alpha_L$ (for LFA-1), $\alpha_M$ (for Mac-1), $\alpha_v$ (for Vibronectin), and from $\beta_1$ to $\beta_7$. Both $\alpha$ and $\beta$ subunits penetrate the cell-membrane lipid bilayer. The integrins are grouped into families: the VLA family (especially including VLA-1 and VLA-4), having the $\beta_1$ subunit; the LEUCAM family, which includes LFA-1 and Mac-1, having the $\beta_2$ subunit; and a group of other integrins having subunits $\beta_3$-$\beta_8$. The type of integrin expressed on the cell surface determines which adhesion molecules (and thus which other cells) the cell will bind, and can be varied in different circumstances. For example, transforming growth factor-$\beta$ increases expression of $\alpha_1\beta_1$, $\alpha_2\beta_1$, $\alpha_3\beta_1$, and $\alpha_5\beta_1$ integrins on fibroblasts and the $\alpha_v\beta_3$ integrin on fibroblasts and osteosarcoma cells; interleukin-1$\beta$ enhances $\beta_1$ expression on osteosarcoma cells; and in response to wounding, the keratinocyte, which normally expresses integrin $\alpha_6\beta_4$, will express $\alpha_5\beta_1$ (VLA-1, the fibronectin receptor) so that the keratinocyte will then migrate over fibronectin in the cell matrix, thus covering the wound.

Integrins generally bind to adhesion molecules in the extracellular matrix. These are molecules expressed on the surface of a cell that mediate the adhesion of the cell to other cells, or to the extracellular matrix. Adhesion molecules are grouped into classes: and include the selectins; the immunoglobulin superfamily, containing ICAM, MadCAM, NCAM, PECAM, and VCAM; the cadherins; and CD44. Adhesion molecules play a part in morphogenesis (e.g., cadherins), and in the treatment of inflammation and wounds (e.g., selectins and the immunoglobulin superfamily).

For purposes of the present invention, although a number of integrins can be utilized in the present invention, the preferred integrins for which modulators are identified in the present invention include, for example, Beta1 integrin (CD29), Beta2 integrin (CD18), AlphaM integrin (CD11b), Beta2 integrin (CD11a), Beta3 integrin (CD61), gpIIIa (a common subunit for alphaIIb and alphaV integrins), AlphaIIb beta3 integrin, CD41/CD61 and glycoprotein.IIb/IIa (gpIIb/IIa). Another integrin of high interest is VLA-4, which is very late antigen 4, CD49d/CD29, $\alpha_4\beta_1$ integrin for which HUTS21 is an appropriate anti-integrin mAbs. LFA-1 is a further integrin of high interest in the present invention for which MEM148 is an appropriate anti-integrin mAbs.

The term "integrin induced epitope" refers to those epitopes (i.e., short chain peptides of approximately 3-15 amino acid units, or 4-13, 4-10 or 4-8 amino acid units) which only become exposed on the integrin molecule and a target for a epitope-binding antibody as otherwise described herein upon the competitive binding of an integrin ligand (agonist or antagonist). There may be one or more epitopes which are exposed upon integrin ligand binding, but usually, the epitope is a single epitope, which is exposure of which is monitored by the present invention.

The term "epitope binding antibody", "ligand induced epitope binding antibody" or "ligand induced integrin epitope binding antibody" refers to an antibody which specifically binds to an epitope on an integrin molecule which becomes exposed upon the binding of a ligand, preferably a competitive ligand of integrin. The antibody may be a polyclonal or monoclonal antibody, but is preferably is a monoclonal antibody which further comprises a reporter molecule or moiety, more preferably a fluorophore as otherwise described herein.

The following epitope binding antibodies (anti-integrin mAbs) are representative of those used in the present invention (see also Table 1, below): Integrin beta1 (Ligand-induced Binding Site, LIBS, CLIBS), activated clone B44; Integrin beta1 (Ligand-induced Binding Site, LIBS, CUBS), activated clone HUTS-4; Integrin beta1 (CD29/β1-integrin), activated clone HUTS-21; Integrin beta1 (CD29/β1-integrin), clone AG89; Integrin beta1 (CD29/β1-integrin), clone 9EG7; Integrin beta2 (Activation epitope), clone MEM-148; Integrin beta2 (Conformationally sensitive epitope), clone MEM-48, Integrin beta2 (Conformationally sensitive epitope), clone KIM185, Integrin beta2 (Conformationally sensitive epitope), clone 127; Integrin alphaM, Mac-1 (CD11B activation epitope), clone CBRM1/5; Integrin alpha1, LFA-1 (CD11a, activation epitope) clone MEM-83; Integrin beta3 (CD61 activation, Ligand-induced Binding Site, LIBS) clone CRC54; and Integrin AlphaIIb beta3, (CD41/CD61, activation epitope), clone PAC-1, among others.

The term "integrin expressing cell" is used to describe a wild-type or engineered cell which expresses on its surface an integrin receptor in an amount or concentration which can be readily used in the assays according to the present invention. Integrin expressing cells include for example, those which are presented in table 1, below. Cells expressing surface integrins may be wild-type (prepared or obtained using standard techniques known in the art), are available commercially or may be prepared readily by engineering cells (including providing hyperproducers of a target integrin) to express surface integrins for analysis. Table 1 below indicates some exemplary cells which are readily available and are useful in the present invention. Preferred integrins used in the present invention include for example, Beta 1 integrin (CD29) which is expressed by human peripheral blood monocytes and lymphocytes including U937 cells, MOLT-4 cells, Jurkat cells, and THP-1 cells; Beta 2 integrin (CD18), which is expressed by human peripheral blood granulocytes, monocytes, lymphocytes including Jurkat cells, HL-60 and JY cells; AlphaM integrin (CD11b), which is expressed by human peripheral blood monocytes including THP-1 cells; Beta2 integrin (CD11a), which is expressed by HL-60 cells; Beta3 integrin (CD61, gpIIIa, a common subunit for alpha1b, alphaV integrins), which is expressed in human platelet cells, including MEG-01 cells and AlphaIIb beta3 integrin (CD41/CD61) glycoprotein IIb/IIa (gpIIb/IIa), which is expressed in human platelets, including MEG-1 cells.

The term "control" or "standard" is used in context to describe the results of an experiment which represents or produces a control or standard against which an experimental result may be compared in order to determine whether a tested event or result has occurred during an experiment. The term "standard" is used to describe a set or reference measurement previously made such that a comparison with a tested sample can be made during a current experiment in order to determine the existence or absence of a result (in this case, the binding of a compound of unknown integrin activity to an integrin receptor to determine whether or not the compound is a competitive ligand, i.e., an agonist or antagonist or an allosteric inhibitor). In the present invention, standards or controls may be determined by taking measurements using normal tissue and/or the absence of experimental tests conditions or disease state or a measurement, among other methods, for which an assay is used. Standards are well known in the art and are determined using well known methods available in the art. Standards may vary from application to application depending upon the assay used and experimental results to be compared to a standard. Controls are similar to standards, but generally are provided contemporaneously with the experiment to be conducted, rather than a priori, in the case of a standard.

For example, in the present invention, the binding of a known competitive ligand to an integrin exposes a ligand induced epitope to which an antibody containing a reporter (preferably a fluorophore as otherwise disclosed herein) is bound. This known activity will provide a measurement of fluorescence as a standard or control for comparing the binding of compounds of unknown integrin activity to the same integrin in the presence of the same antibody. An experimental result which produces antibody binding and fluorescence similar in intensity to the control or standard will evidence that a compound of unknown integrin activity is a competitive ligand of the integrin which was assayed. Additional controls may include measurements of the non-specific binding of an integrin ligand induced epitope binding antibody to the assayed integrin in the absence of a ligand. This control will provide a measurement of the background binding to compare experimental results. In experiments to determine whether compounds of unknown integrin activity are allosteric inhibitors of an integrin, a control or standard may include a measurement of the ligand induced epitope binding of an antibody in the presence of a known ligand of integrin, as well as the non-specific binding of the same antibody to the assayed integrin in the absence of ligand.

| Integrin | Anti-integrin mAbs | Vendor, catalog number | Cells, vendor, catalog number |
|---|---|---|---|
| Beta1 integrin: CD29, is a common subunit for alpha1-11, alphaV integrins | Integrin beta1 (Ligand-induced Binding Site, LIBS, CLIBS), activated clone B44 | EMD Millipore, MAB2259Z | Human peripheral blood monocytes, lymphocytes, U937, ATCC CRL-1593.2, THP-1, ATCC TIB-202 |
| Beta1 integrin: CD29 | Integrin beta1 (Ligand-induced Binding Site, LIBS, CLIBS), activated clone HUTS-4 | EMD Millipore, MAB2079Z | U937, ATCC CRL-1593.2, THP-1, ATCC TIB-202 |
| Beta1 integrin: CD29 | Integrin beta1 (CD29/β1-Integrin), clone HUTS-21 | BD Pharmingen, 556048 | MOLT-4, ATCC CRL-1582; U937, ATCC CRL-1593.2 |

-continued

| Integrin | Anti-integrin mAbs | Vendor, catalog number | Cells, vendor, catalog number |
|---|---|---|---|
| Beta1 integrin: CD29 | Integrin beta1 (CD29/β1-Integrin), clone AG89 | MBL International, D050-5 | MOLT-4, ATCC CRL-1582; Jurkat, ATCC TIB-152 |
| Beta1 integrin: CD29 | Integrin beta1 (CD29/β1-Integrin), clone 9EG7 | BD Pharmingen, 553715 | U937, ATCC CRL-1593.2, THP-1, ATCC TIB-202 |
| Beta2 integrin: CD18, is a common subunit for alphaL, alphaM, alphaX, alphaD integrins | Integrin beta2 (Activation epitope), clone MEM-148 | AbD Serotec, MCA2086PE | Human peripheral blood granulocytes, monocytes, lymphocytes, Jurkat, ATCC TIB-152 |
| Beta2 integrin: CD18 | Integrin beta2 (Activation epitope), clone MEM-148 | LifeSpan BioSciences, LS-C44253-1000 | Human peripheral blood granulocytes, monocytes, lymphocytes, HL-60, ATCC CCL-240, Jurkat, ATCC TIB-152 |
| Beta2 integrin: CD18 | Integrin beta2 (Conformationally sensitive epitope), clone MEM-48 | Gen-Probe, Inc., 852.542.010 | JY, ATCC 77441, Jurkat, ATCC TIB-152 |
| Beta2 integrin: CD18 | Integrin beta2 (Conformationally sensitive epitope), clone KIM185 | ATCC, CRL-2839 | JY, ATCC 77441, Jurkat, ATCC TIB-152 |
| Beta2 integrin: CD18 | Integrin beta2 (Conformationally sensitive epitope), clone 127 | ATCC, CRL-2838 | JY, ATCC 77441, Jurkat, ATCC TIB-152 |
| AlphaM integrin: CD11b | Integrin alphaM, Mac-1, (CD11b activation epitope), clone CBRM1/5 | eBioscience, Inc., 12-0113-42 | Human peripheral blood monocytes, THP-1, ATCC TIB-202 |
| Beta2 integrin: CD11a | Integrin alphaL, LFA-1 (CD11a, activation epitope), clone MEM-83 | GeneTex, Inc., GTX23981 | HL-60, ATCC CCL-240 |
| Beta3 integrin: CD61, gpIIIa, is a common subunit for alphaIIb, alphaV integrins | Integrin beta3, (CD61 activation, Ligand-induced Binding Site, LIBS) clone CRC54 | Abcam, ab34409 | Human platelets, MEG-01, ATCC CRL-2021 |
| AlphaIIb beta3 integrin, CD41/CD61, glycoprotein IIb/IIIa (gpIIb/IIIa), | Integrin AlphaIIb beta3, (CD41/CD61, activation epitope), clone PAC-1 | BD Pharmingen, 340507 | Human platelets, MEG-01, ATCC CRL-2021 |

The term "specific binding" or "specifically binds" refers to two molecules in this case, an integrin molecule and a ligand, forming a complex that is relatively stable under physiological conditions. Specific binding is characterized by a high affinity and a low to moderate capacity as distinguished from "nonspecific binding" which usually has a low affinity with a moderate to high capacity. Typically, binding is considered specific when the difference between the dissociation constant ($K_d$) for a target cell is at least 1000-fold less than the $K_d$ for a control, non-target cell. If necessary, nonspecific binding may be reduced without substantially affecting specific binding by varying the binding conditions.

The term "neoplasia" or "neoplasm" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and may invade surrounding tissues. As used herein, the term neoplasia/neoplasm is used to describe all cancerous disease states and embraces or encompasses the pathological process associated with cancer, in particular hematopoietic neoplasm and its metastasis. A hematopoietic neoplasm is a neoplasm of hematopoeitic cells of the blood or lymph system and includes disease states such as Hodgkin's disease, non-Hodgkin's lymphoma, leukemias, including non-acute and acute leukemias, such as acute myelogenous leukemia, acute lymphocytic leukemia, acute promyelocytic leukemia (APL), adult T-cell leukemia, basophilic leukemia, eosinophilic leukemia, granulocytic leukemia, hairy cell leukemia, leukopenic leukemia, lymphatic leukemia, lymphoblastic leukemia, lymphocytic leukemia, megakaryocytic leukemia, micromyeloblastic leukemia, monocytic leukemia, neutrophilic leukemia and stem cell leukemia.

Other cancers which may be diagnosed and/or treated/prevented (especially including the metastasis of the cancer) using methods and/or compounds/pharmaceutical compositions according to the present invention include, for example, carcinomas (e.g., squamous-cell carcinomas, adenocarcinomas, hepatocellular carcinomas, and renal cell carcinomas), particularly those of the bladder, bowel, breast, cervix, colon, esophagus, head, kidney, liver, lung, neck, ovary, pancreas, prostate, and stomach; leukemias (including as otherwise described hereinabove); benign and malignant lymphomas, particularly Burkitt's lymphoma and Non-Hodgkin's lymphoma; benign and malignant melanomas; myeloproliferative diseases; sarcomas, particularly Ewing's sarcoma, hemangiosarcoma, Kaposi's sarcoma, liposarcoma, myosarcomas, peripheral neuroepithelioma, and synovial sarcoma; tumors of the central nervous system (e.g., gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas); germ-line tumors (e.g., bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, cutaneous cancer, including basal cell carcinoma and squamous cell carcinoma and melanoma; mixed types of neoplasias, particularly carcinosarcoma and Hodgkin's disease; and tumors of mixed origin, such as Wilms' tumor and teratocarcinomas, especially including the metasis of any one or more of these cancers in a patient in need thereof.

The term "prophylactic" "prevention" or "reducing the likelihood" is used to describe the use of a compound described herein which either prevents or reduces the likelihood of a condition or disease state in a patient or subject, especially including, for example, the metastasis of a cancer.

The term "pharmaceutically acceptable" refers to a salt form of the present compounds or, a carrier, additive or excipient which is not unacceptably toxic to the subject to which it is administered.

The term "integrin mediated disease" is used throughout the specification to describe a disease which is mediated through or occurs as a consequence of the actions or interactions of integrin. Representative disease states and/or disorders (conditions) which may be treated by the present invention include, for example, nervous system diseases and/or disorders including; for example, multiple sclerosis, myasthenia gravis, neuropathy, uveitis; circulatory system diseases and/or disorders including hemolytic anemia, pernicious anemia, thrombocytopenia, temporal arteritis, antiphospholipid syndrome, Wegener's granulomatosis, Behcet's disease; musculoskeletal diseases and/or disorders including rheumatoid arthritis, scleroderma, spondyloarthropathies, Sjogren's dyndrome, systemic lupus erythematosus, polymyositis dermatomyositis, ankylosing spondylitis; gastrointestinal system diseases and/or disorders including Crohn's disease, primary biliary cirrhosis, hepatitis (B and/or C), ulcerative colitis; endocrine system diseases and/or disorders including diabetes mellitus (type 1), Grave's disease, Hashimoto's thyroiditis, oophoritis; skin diseases and/or disorders including psoriasis, dermatitis herpetiformis, pemphigus vulgaris, vitiligo; and respiratory diseases and/or disorders including asthma. See, for example, Jackson, D. Y., *Curren Pharm Des*, 8:1229-1253 (2002).

In particular, the present invention may be used to treat or reduce the likelihood of integrin-mediated diseases including arthritis, rheumatoid arthritis, osteoarthritis, diseases or conditions resulting from non-specific immune responses such as adult respiratory distress syndrome, shock, oxygen toxicity, septic shock, multiple organ injury syndrome secondary to septicemia, multiple organ injury syndrome secondary to trauma, ischemia-reperfusion injury, reperfusion injury of tissue due to cardiopulmonary bypass, myocardial infarction or use with thrombolysis agents to liquidize or eliminate thrombus, acute glomerulonephritis, vasculitis, reactive arthritis, dermatosis with acute inflammatory components, stroke, thermal injury, hemodialysis, leukapheresis, ulcerative colitis, necrotizing enterocolitis and granulocyte transfusion associated syndrome, solid organ transplant rejection, autoimmune diseases including Raynaud's syndrome, autoimmune thyroiditis, dermatitis, multiple sclerosis, arthritis, including rheumatoid arthritis and osteoarthritis, insulin-dependent diabetes mellitus, diabetes retinopathy, uveitis, inflammatory bowel disease including Crohn's disease and ulcerative colitis, and systemic lupus erythematosus, hyperproliferative diseases such as psoriasis, hyperkeratosis, ichthyosis, keratoderma, lichen planus or warts, hematopoietic neoplasms and metastasis of such neoplasms, including Hodgkin's disease, non-Hodgkin's lymphoma, leukemias, including non-acute and acute leukemias, such as acute myelogenous leukemia, acute lymphocytic leukemia, acute promyelocytic leukemia (APL), acute T-cell lymphoblastic leukemia, adult T-cell leukemia, basophilic leukemia, eosinophilic leukemia, granulocytic leukemia, hairy cell leukemia, leukopenic leukemia, lymphatic leukemia, lymphoblastic leukemia, lymphocytic leukemia, megakaryocytic leukemia, micromyeloblastic leukemia, monocytic leukemia, neutrophilic leukemia and stem cell leukemia; as well as other cancers as otherwise described herein and in adjunct therapy in reducing the likelihood of retinoic acid syndrome in an acute promyelocytic leukemia (APL) patient being treated with retinoic acid, among others.

The term "reporter" or "reporter moiety" is used to described any moiety which can be linked to an integrin epitope specific monoclonal antibody as otherwise described herein and which can be used to identify the monoclonal antibody and in particular, its binding to an epitope on integrin. While any reporter may be used in the present invention which is consistent with the assays according to the present invention, reporters include fluorophores. The fluorophore label used in conjunction with the present invention is a fluorescent moiety. Suitable fluorophores include, but are not limited to, fluorescein, isothiocyanate, rhodamine, phycoerythrin, phycocyanin, allophycocyanin, ophthaldehyde label, fluorescamine, tetramethylrhodamine, dipyrrometheneboron difluoride dyes (available from Molecular Probes, Inc, among others), near infrared dyes, lanthanide chelates, or analytes bearing such fluorescent moieties. Where the labeling of an antibody is desired, fluorescein labels may preferably be used. Such a labeled antibody may be used in direct immunoassays for protein species present at concentrations of approximately 1-10 micromolar. Any suitable method known to those skilled in the art may be used to directly label the analytes of binding partners of the present invention.

Compounds (integrin ligands or allosteric/non-canonical inhibitors of integrin) which are identified according to the present invention are suitable for pharmaceutical use and administration to patients. A typical pharmaceutical composition comprises a compound, as otherwise described herein, in combination with at least one pharmaceutically acceptable carrier, additive or excipient.

A pharmaceutical composition is formulated to be compatible with its intended route of administration. Methods to accomplish the administration are known to those of ordinary skill in the art. Examples of administration of a pharmaceutical composition according to the present invention include, for example, oral ingestion, inhalation, intravenous, intraperitoneal, intramuscular, intracavity, subcutaneous, cutaneous, or transdermal.

Solutions or suspensions used for cutaneous or subcutaneous application typically include at least one of the following components: a sterile diluent such as water, saline solution, fixed oils, polyethylene glycol, glycerine, propylene glycol, or other synthetic solvents; antibacterial agents, such as benzyl alcohol or methyl parabens; antioxidants, such as ascorbic acid or sodium bisulfite; chelating agents, such as ethylenediaminetetraacetic acid (EDTA); buffers such as acetate, citrate, or phosphate; and tonicity agents, such as sodium chloride or dextrose. The pH of the composition can be adjusted readily with pharmaceutically acceptable acids or bases. Such preparations may be enclosed in ampoules, disposable syringes, or multiple dose vials.

Solutions or suspensions used for intravenous administration include a carrier such as physiological saline, bacteriostatic water, Cremophor EL™ (BASF, Parsippany, N.J.), ethanol, or polyol. In all cases, the composition must be sterile and fluid for easy syringability. Proper fluidity can often be obtained using lecithin or surfactants. The composition must be stable under the conditions of manufacture and storage. Microorganism growth can be prevented using antibacterial and antifungal agents, e.g., parabens, chlorobutanol, phenol, ascorbic acid, etc. In many cases, isotonic agents (sugar), polyalcohols (mannitol and sorbitol), or sodium chloride may be included in the composition. Prolonged absorption of the composition can be accomplished by adding an agent which delays absorption, e.g., aluminum monostearate and gelatin.

Oral compositions include an inert diluent or edible carrier. The composition can be enclosed in gelatin or compressed into tablets. For the purpose of oral administration, the compounds can be incorporated with excipients and placed in tablets, troches, or capsules. Pharmaceutically compatible binding agents or adjuvant materials can be included in the composition. The tablets, troches; and capsules, may contain (1) a binder such as microcrystalline cellulose, gum tragacanth or gelatin; (2) an excipient such as starch or lactose, (3) a disintegrating agent such as alginic acid, Primogel, or corn starch; (4) a lubricant such as magnesium stearate; (5) a glidant such as colloidal silicon dioxide; or (6) a sweetening agent or a flavoring agent.

The pharmaceutical composition according to the invention also may be administered by a transmucosal or transdermal route. Transmucosal administration can be accomplished through the use of lozenges, nasal sprays, inhalers, or suppositories. Transdermal administration can also be accomplished through the use of a composition containing ointments, salves, gels, or creams known in the art. For transmucosal or transdermal administration, penetrants appropriate to the barrier to be permeated are used. For administration by inhalation, the compounds according to the present invention can be delivered in an aerosol spray from a pressured container or dispenser, which contains a propellant (e.g., liquid or gas) or a nebulizer.

The compounds according to the present invention are administered in therapeutically-effective amounts as described. Therapeutically effective amounts vary as a function of the disease to be treated, the subject's age, condition, sex, size and severity of medical condition. Appropriate dosage may be determined by a physician based on clinical indications. The compound-containing composition may be given as a bolus dose to maximize the circulating levels of the compounds for the greatest length of time. Continuous infusion may also be used after the bolus dose.

Non-limiting examples of dosage ranges that can be administered to a subject can be chosen from: 1 µg/kg to 20 mg/kg, 1 µg/kg to 10 mg/kg, 1 µg/kg to 1 mg/kg, 10 µgkg to 1 mg/kg, 10 µg/kg to 100 µg/kg, 100 µg/kg to 1 mg/kg, 250 µgkg to 2 mg/kg, 250 µgkg to 1 mg/kg, 500 µs/kg to 2 mg/kg, 500 µg/kg to 1 mg/kg, 1 mg/kg to 2 mg/kg, 1 mg/kg to 5 mg/kg, 5 mg/kg to 10 mg/kg, 10 mg/kg to 20 mg/kg, 15 mg/kg to 20 mg/kg, 20 mg/kg to 25 mg/kg, 15 mg/kg to 25 mg/kg, 20 mg/kg to 25 mg/kg, and 20 mg/kg to 30 mg/kg (or higher). These dosages may be administered daily, weekly, biweekly, monthly, or less frequently, for example, biannually, depending on dosage, method of administration, disorder or symptom(s) to be treated, and individual subject/patient characteristics, as well as the pharmacokinetics and bioavailability of the compounds. Dosages can also be administered via continuous infusion (e.g., through a pump or other medical device). The administered dose depends upon depend on the route of administration and the pharmacokinetics of the compounds as well as the agents which are incorporated with the compound. For example, subcutaneous administration may require a higher dosage than intravenous administration.

In certain instances, it may prove to be advantageous to formulate compositions in dosage unit form for ease of administration and uniformity of dosage. Dosage unit form as refers to physically discrete units of pharmaceutical composition suited for the patient to be administered at a point in time. Each dosage unit contains a predetermined quantity of compound calculated to produce a therapeutic effect in association with the carrier, additive or excipient. The dosage unit depends on the characteristics of the compounds and the particular therapeutic effect to be achieved.

Toxicity and therapeutic efficacy of the composition can be determined readily by standard pharmaceutical procedures in cell cultures or experimental animals. e.g. by determining the $LD_{50}$ (the dose lethal to 50% of the population) and the $ED_{50}$ (the dose therapeutically effective in 50% of the population). The dose ratio between toxic and therapeutic effects is the therapeutic index, which can be expressed as the ratio $LD_{50}/ED_{50}$.

Data obtained from cell culture assays and animal studies can be used to formulate a dosage range in humans. The dosage may vary within this range depending upon the composition used and the route of administration. For any compound used in the methods described herein, the therapeutically effective dose can be estimated initially using cell culture assays. Animal models can be used to determine circulating plasma concentrations and $IC_{50}$ values (i.e., the concentration of compounds that achieves a half-maximal inhibition of symptoms). The effects of any particular dosage can be monitored by a suitable bioassay.

The cell based assay(s) according to the present invention is readily adapted to high throughput screening, especially when coupled to HyperCyt™, a preferred system. Cell based screening is compatible with a search for ligands for integrin receptors using flow cytometry, especially high throughput flow cyometry. The present invention employs a flow cytometry device to perform measurements of the formation of complexes in a moving liquid stream. In the flow cytometry device, a liquid stream forming a sheath fluid into which a sample is introduced is focused through an orifice. As the objects pass through the orifice, particular characteristics of the objects are determined based upon the analyzing or counting capabilities of the flow cytometry device. Typically, the flow cytometry device used with the present invention is capable of sorting or counting at high speeds, collecting tens of thousands of objects.

Although many conventional flow cytometry devices may be used in the method of the present invention, one commercially available conventional flow cytometer is the FACScan™ instrument sold by Becton Dickinson Immunocytometry Systems, San Jose, Calif., which relies on a hydrodynamically focused fluid system. The FACScan™ instrument rapidly analyzes cells on the basis of fluorescence and light scatter properties. Analysis is accomplished by introducing cells in a suspension to the center of a focused liquid stream thus causing them to pass, one at a time, through a focused light from a high powered laser. Each cell is individually characterized by its light scatter signals and by the intensity and color of fluorescence emitted while it is illuminated. This system is described in U.S. Pat. No. 4,844,610 issued Jul. 4, 1989 to North, U.S. Pat. No. 5,030,022 issued Jul. 9, 1991 to North and U.S. Pat. No. 5,040,890 issued Aug. 20, 1991 to North, the entire contents and disclosures of which are hereby incorporated by reference. Other approaches for using high throughput flow cytometry are also available in the art, or as otherwise taught herein.

The invention is described further in the following example, which is illustrative only and in no way limiting.

Materials and Methods

Materials—

The VLA-4 specific ligand 4-((N'-2-methylphenyl)ureido)-phenylacetyl-L-leucyl-L-aspartyl-L-valyl-L-prolyl-L-alanyl-L-alanyl-L-lysine (LDV), and its FITC-conjugated analog (LDV-FITC) were synthesized at Commonwealth Biotechnologies (Richmond, Va.). Mouse anti-human CD29, HUTS-21(PE), isotype control (mouse IgG2a κ PE) clone G155-178 were purchased from BD Biosciences (San Jose, Calif.) and used according to manufacturer instructions. N-(2, 6-dichlorobenzoyl)-(L)-4-(2',6'-bis-methoxyphenyl)phenylalanine (TR-14035) compound was synthesized by Dr. Wei Wang (Department of Chemistry, University of New Mexico). Two recently identified VLA-4 ligands 3-(adamantane-1-carbonylamino)-3-(4-ethoxyphenyl) propanoic acid and 3-(adamantane-1-carbonylamino)-3-(4-propoxyphenyl) propanoic acid (SID: 14732971, CID: 5197400; and SID: 14732972, CID: 4329131) were from NIH MLSMR (http://pubchem.ncbi.nlm.nih.gov/) curated by BioFocus/DPI (South San Francisco, Calif.). All other reagents were from Sigma-Aldrich (St. Louis, Mo.). Stock peptide solutions were prepared in DMSO, at concentrations ~1000 fold higher than the final concentration. Usually, 1 µl of stock solution was added to 1 ml of cell suspension yielding a final DMSO concentration of 0.1%. Control samples were treated with equal amount of pure DMSO (vehicle).

Cells—

The human histiocytic lymphoma cell line U937 was purchased from ATCC (Manassas, Va.). Cells were grown at 37° C. in a humidified atmosphere of 5% $CO_2$ and 95% air in RPMI 1640 (supplemented with 2 mM L-glutamine, 100 units/mL penicillin, 100 µg/mL streptomycin, 10 mM HEPES, pH 7.4, and 10% heat inactivated fetal bovine serum). Cells were then harvested and resuspended in 1 ml of HEPES buffer (110 mM NaCl, 10 mM KCl, 10 mM glucose, 1 mM $MgCl_2$, 1.5 mM $CaCl_2$ and 30 mM HEPES, pH 7.4) containing 0.1% HSA and stored on ice. Cells were counted using the Coulter Multisizer/Z2 analyzer Beckman Coulter (Miami, Fla.). For experiments, cells were suspended in the same HEPES buffer at $10^6$ cells/ml and warmed to 37° C. for 10 min prior to binding experiments (see below).

LDV-FITC Competitive Binding Assay—

Cells in HEPES buffer containing 1 mM $MgCl_2$, 1.5 mM $CaCl_2$ were preincubated with different concentration of compounds, 1 µM unlabeled LDV (control) or DMSO (vehicle) for 20-30 min at room temperature. Next, LDV-FITC was added to the cells/compound mix (10 nM final concentration), and cell were incubated for additional 30-40 min. FITC fluorescent (FL1 channel) was measured using BD FACScan flow cytometer collecting 5000 events. The data were plotted as LDV-FITC specific binding vs. the concentration of competitor and the data were fitted to a one site competition equation. The equilibrium dissociation constant, $K_i$, was calculated using Cheng and Prusoff equation ($K_d$ for LDV-FITC ~12 nM, labeled ligand concentration ~10 nM).

HUTS-21 Antibody Binding—

U937 cells were suspended in the HEPES buffer (see above) $1 \times 10^6$ cells/ml, 100 µl aliquots ($10^5$ cells) were incubated with different concentrations of unlabeled compounds for 10 min. Next, 20 µl of PE-labeled HUTS-21 antibodies was added and cells were incubated for additional 30-40 mM at room temperature. Next, cells were washed with 1 ml of HEPES buffer, resuspended in 300-500 µl of buffer and analyzed by flow cytometry (FL2 channel, BD FACScan). The data were plotted as mean channel fluorescence vs. the concentration of the compound. The data were fitted to a sigmoidal dose-response equation. To determine the level of non-specific binding, cells were stained in parallel with the isotype control antibodies.

Statistical Analysis—

Curve fits, statistics, and Ki calculations were performed using GraphPad Prism version 4.00 for Windows, GraphPad Software, (San Diego, Calif.), see the website at graphpad.com (www.graphpad.com). Each experiment was repeated at least two times. The experimental curves represent the mean of two or more independent runs. Standard error of the mean was calculated using GraphPad Prism.

Discovery of VLA-4 Ligands. The Flow Cytometric Screen for VLA-4 is Reported in PubChem.

In brief, in 384 well plates prepared with Jurkat cells and delivered by HyperCyt platform to the flow cytometer, we could discriminate cell autofluorescence, the two fold increase of fluorescence of ligand bound to resting cells and an additional two fold increase in ligand binding when the cells were treated with $Mn^{+2}$ which increased the affinity of VLA-4 as well as ligand binding. The Z' for the screen of ~25,000 compounds was ~0.7 (AIDs 528, 529, 576, 702, 703). While the screen was intended to identify allosteric ligands for VLA-4, small molecules that blocked LDV-FITC binding in either the presence or the absence of $Mn^{+2}$ were identified as competitive inhibitors at both 4° and 37°.

Post screening analysis of the inhibitors detected in primary screening was performed by using MESA Analytics & Computing clustering software package (Santa Fe, N. Mex.). The MDL 320 fingerprint keys were used to represent the chemical compounds. Clustering at various similarity thresholds was done in order to select the most appropriate similarity threshold. The most potent inhibitor clusters were selected for follow up. The most potent inhibitors (MLS000085920, MLS000044001, and MLS000085916, see FIG. 1) formed the basis of virtual screening of MLSMR library. The maximum common substructure for the selected cluster was used as a query in virtual screening of the compound library. The most similar compounds were identified and the compounds were subsequently retested in dose response in the LDV-FITC dose-response assay described above. The compounds with the best activity are also included in FIG. 1, MLS000521558, and MLS000521553.

Homology Modeling and Docking—

To verify a common mode of binding to the VLA-4 binding site we built a homology model for the headpiece of the VLA-4 integrin, which comprises the beta-propeller from the alpha subunit and the I-like domain from the beta subunit. The homology model was built using the SWISS-MODEL server, based on the X-ray structure of αVβ3 integrin complexed with a ligand containing the RGD motif (Protein Data Bank, http://www.rcsb.org, PDB access code: 1L5G). For sequence alignment, the T-coffee program was used and the model obtained was further refined manually to avoid deletions or insertions in the conserved regions. Finally, manganese ions (MIDAS, ADMIDAS and LIMBS) have been added into the VLA-4 binding site with the same atomic coordinates as in the αVβ3 structure. At the final step, the model has been minimized to reduce the steric clashes of the side chains without changing the backbone of the integrin.

Docking studies were carried out using FRED (OpenEye Scientific Software, Santa Fe, USA, FRED, http://www.eyesopen.com/products/applications/fred.html), which uses a pre-computed database of conformations for a given ligand. Multi-conformer databases were generated using OMEGA (OpenEye Scientific Software, Santa Fe, USA, Omega, http://www.eyesopen.com/products/applications/omega.html) with default parameters which produced an average of 150 conformers per ligand. Docking simulations were performed with default parameters, and each ligand conformer was rigidly minimized based on shape and chemical complementarity to the protein binding site. The grid-box was defined by increasing the size of RGD crystallized ligand by 5 Å on each side of the ligand. This procedure was found suitable to allow a number of compounds to fit into the binding site.

Results

Figure 2:
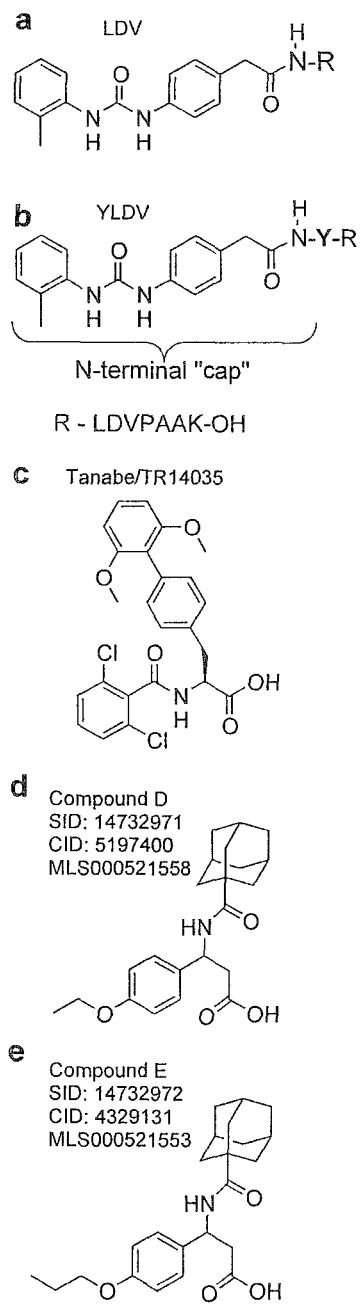
FIG. 2 shows structure of compounds used in the study: (a) 4-((N-2-methylphenyl) ureido)-phenylacetyl-L-leucyl-L-aspartyl-L-valyl-L-prolyl-L-alanyl-L-alanyl-L-lysine, LDV compound, based upon BIO-1211; (b) YLDV compound, additional L-tyrosine is shown in bold; (c) N-(2,6-dichlorobenzoyl)-(L)-4-(2',6'-bis-methoxyphenyl)phenylalanine, TR14035; (d) Recently identified VLA-4 ligand, 3-(adamantane-1-carbonylamino)-3-(4-ethoxyphenyl) propanoic acid, SID: 14732971, CID: 5197400; compound D; (e) VLA-4 ligand, 3-(adamantane-1-carbonylamino)-3-(4-propoxyphenyl) propanoic acid, SID: 14732972, CID: 4329131, compound E. In compound LDV, the peptide designated R is LDVPAAKOH (SEQ ID NO: 1) and in compound YLDV, the peptide designated YR is YLDVPAAKOH (SEQ ID NO: 2). Note that KOH in SEQ ID NO:1 and SEQ ID NO:2 stands for hydroxylysine (HYL).

Below is described the results of an exemplary embodiment of the present invention and should not be read as limiting. From one embodiment, we have reported in PubChem a screen using a fluorescent ligand for VLA-4 in a homogeneous flow cytometry assay that identified novel inhibitors of VLA-4. Because of the relatively low signal-background ratio of that assay (~2/1), embodiments explore alternatives for detecting and characterizing small molecule interactions. Ligand induced binding sites (LIBS) are antibody epitopes that become exposed after a conformational change within an integrin molecule due to ligand binding. LIBS can be detected using conformationally sensitive mAbs that are commercially available for several integrins. We hypothesized that LIBS could quantitatively report the occupancy of the integrin ligand binding pocket by an unlabeled integrin ligand. To verify this idea certain embodiments have employed several small VLA-4 ligands with both previously reported and unknown binding affinities (FIG. 2).

An LDV small molecule (and its fluorescent analog, LDV-FITC, (FIG. 2, panel a)) are well characterized VLA-4 ligands that have been used in several laboratories to detect VLA-4 affinity and conformational changes. Here, embodiments can use LDV-FITC as a labeled competitor to determine binding affinities ($K_i$) of other unlabeled ligands. The unlabeled LDV can be used both as positive control for the induction of LIBS as well as a blocking compound to detect the level of non-specific binding in the competitive binding assay. The YLDV compound can have an additional tyrosine residue between its N-terminal "cap" and LDV sequence (FIG. 2, panel b). This modification decreased its binding affinity ~100 fold (FIG. 4, panel a). TR14035 (FIG. 2, panel c) is described in the literature as a potent ligand that blocks VLA-4 binding to VCAM-1. Compounds D and E (FIG. 2, panel d, e) are two novel VLA-4 ligands discovered in a high-throughput screen at the University of New Mexico Center for Molecular Discovery (http://pubchem.ncbi.nlm.nih.gov, AID: 529, 702).

Binding of an Unlabeled LDV-Containing Small Molecule Induces Exposure of Huts-21 Epitope with $EC_{50}$ Identical to $K_d$ for LDV-FITC Binding The design of the LDV-containing small molecule (FIG. 2, panel a) was based upon the published structure of BIO-1211 (Biogen) compound, which has been shown to induce LIBS. The small changes in the structure of the molecule (two alanine and one lysine residues added in a region suggested by SAR to be outside of the binding pocket) have not altered its ability to induce LIBS.

As shown in (FIG. 3, panel a), the binding of conformationally sensitive mAbs was well behaved. Flow cytometric histograms were symmetrical and histogram peaks shifted to the right with increasing unlabeled ligand concentration. The signal to background ratio was about 10/1. Binding of isotype control mAbs was identical to the binding of HUTS-21 in the absence of the ligand (data not shown). The histogram showing binding of HUTS-21 at 0.1 nM LDV is at the same level as non-specific mAb binding. Thus, in the absence of the ligand no HUTS-21 epitope exposure was observed. The concentration dependent dose-response for LIBS correlated well with ligand occupancy for LDV-FITC small molecule for both low and high affinity states of VLA-4 (FIG. 3, panel b for low affinity and). The $EC_{50}$ for the induction of epitope exposure was identical to the previously published dissociation constant ($K_d$) for the fluorescent LDV analog (LDV-FITC). Thus, quantitatively the number of ligand occupied binding sites is reflected in the number of bound mAbs and LIBS sites. As the total concentration of VLA-4 receptors in solution was <0.1 nM, these experiments were performed under conditions at which no significant ligand depletion has been observed. Taken together, these data suggest that the LIBS dose-response reflects the binding affinities for unlabeled integrin.

Two Known VLA-4 Ligands Compete with LDV-FITC for Binding to VLA-4 and Induce HUTS-21 Epitope Exposure Similar to an LDV-Containing Small Molecule Next, we took advantage of LIBS detection to examine the binding of two previously characterized unlabeled VLA-4 ligands (FIG. 2, panel b and c). Whereas YLDV is low affinity, TR14035 (Tanabe, FIG. 2, panel c) is reported to be a highly potent inhibitor of VLA-4 binding to VCAM-1. Although this compound is reported as non-selective α4β1/α4δ7-ligand, since U937 cells do not express significant amounts of the β7-integrin subunit, the data presented here can be interpreted in terms of binding to VLA-4. To characterize the binding affinities of these compounds we performed competitive equilibrium binding experiments (FIG. 4, panel a). Cells were incubated in the presence of 10 nM LDV-FITC with increasing concentrations of each compound. The resulting sigmoidal dose-response curves were fitted using the Cheng-Prusoff equation to determine $K_i$ (which is analogous to a dissociation constant $K_d$) from the $EC_{50}$ (FIG. 4, panel a).

In parallel, HUTS-21 binding experiments were performed (FIG. 4, panel b, analogous to FIG. 3, panel b). A saturating amount of LDV (1 µM LDV>>Kd (12 nM)) was used as a positive control. The resulting curves were fitted to a sigmoidal dose-response binding equation, in which the Hill slope was generally close to 1.0. $EC_{50}$s for the induction of HUTS-21 epitope exposure were similar to $K_i$ values determined in a competition experiment (compare FIG. 4, panel a, and b). Introduction of the additional tyrosine into LDV sequence lowered the binding affinity of the compound by about two orders of magnitude (compare $EC_{50}$ for LDV and YLDV in FIGS. 3 and 4). Also, as shown for other VLA-4 ligands, the binding of TR14035 was strongly dependent upon the presence of divalent ions ($Mn^{2+}$) (data not shown), and its binding affinity was similar to the previously published $IC_{50}$ for ligand binding. Thus, as for LDV, YLDV and TR14035 resulted in the LIBS exposure, and the occupancy of the ligand binding pocket is reported by HUTS-21 antibody binding.

Figure 5:
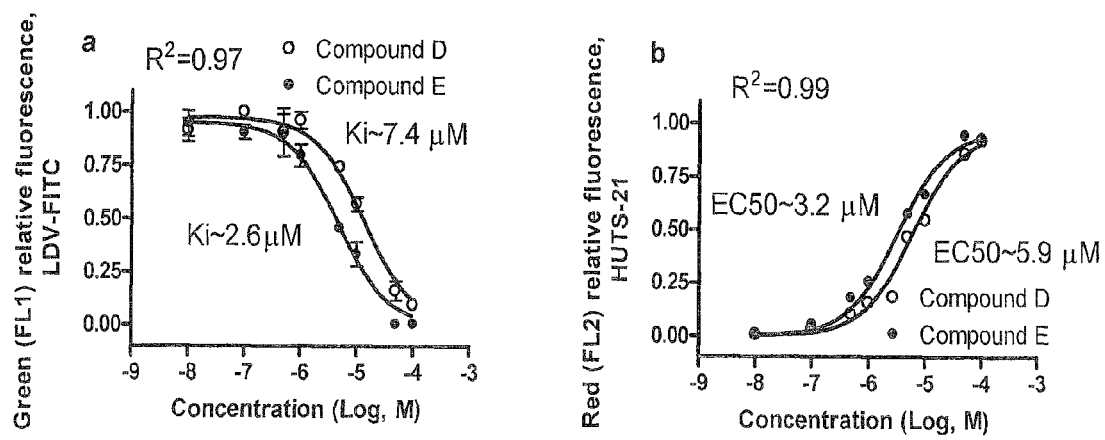
FIG. 5 shows competition between novel VLA-4 ligands and LDV-FITC ligand, and their effect upon HUTS-21 epitope exposure. a) Competitive binding of LDV-FITC ligand to U937 cells in the presence of different concentrations of Compound D or Compound E (FIG. 2, panel d, e). b) Binding of HUTS-21 to cells in the presence of different concentrations of Compound D or Compound E (FIG. 2, panel d, e).

Two Novel Compounds Compete for LDV-FITC Binding and Induce HUTS-21 Epitope Exposure Recently, through a screen based on LDV-FITC binding and virtual screening follow-up, we have identified a number of compounds that inhibit LDV-FITC binding (PubChem BioAssay AID #529, 702). Two of the selected compounds (D and E, FIG. 2, panel d, and e) in the presence of 0.5 mM $Mn^{2+}$ exhibited nanomolar affinity in an LDV-FITC competitive binding assay ($EC_{50}$=90 nM leading to $K_i$~20 nM) (AID #702 confirmatory, concentration-response relationship). To verify that these novel compounds involved the same mechanism of binding interaction, we evaluated the LIBS response in the absence of $Mn^{2+}$. The two VLA-4 ligands showed similar affinities in both the LDV-FITC competition and the HUTS-21 binding assays (FIG. 5). Once again, $EC_{50}$ values for HUTS-21 binding correlated with $K_i$s determined in the competition assay with LDV-FITC.

Figure 6:
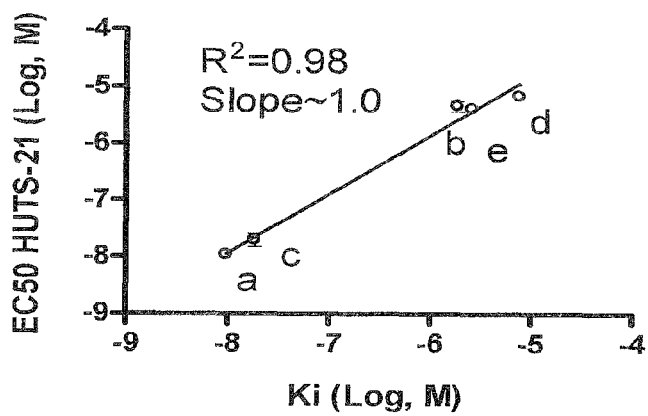
FIG. 6 shows $EC_{50}$ for HUTS-21 binding (determined in the HUTS-21 binding experiments as shown in FIG. 4, panel b and FIG. 5, panel b) plotted vs. $K_i$ (determined in the competition assay with LDV-FITC as shown in FIG. 4, panel a and FIG. 5, panel a) for the five compounds studied.

Correlation Between EC50 for HUTS-21 Binding and $K_i$ Determined in the Competition Assay The data is summarized as a plot of $EC_{50}$s for HUTS-21 binding vs. $K_i$s determined in the competition assay with LDV-FITC (FIG. 6). A strong correlation between $K_i$ and $EC_{50}$ is observed for the five ligands studied. Thus, conformationally sensitive anti-$\beta_1$-integrin mAbs can be used to determine binding affinities of unlabeled VLA-4 integrin ligands.

Docking Results

Figure 7:
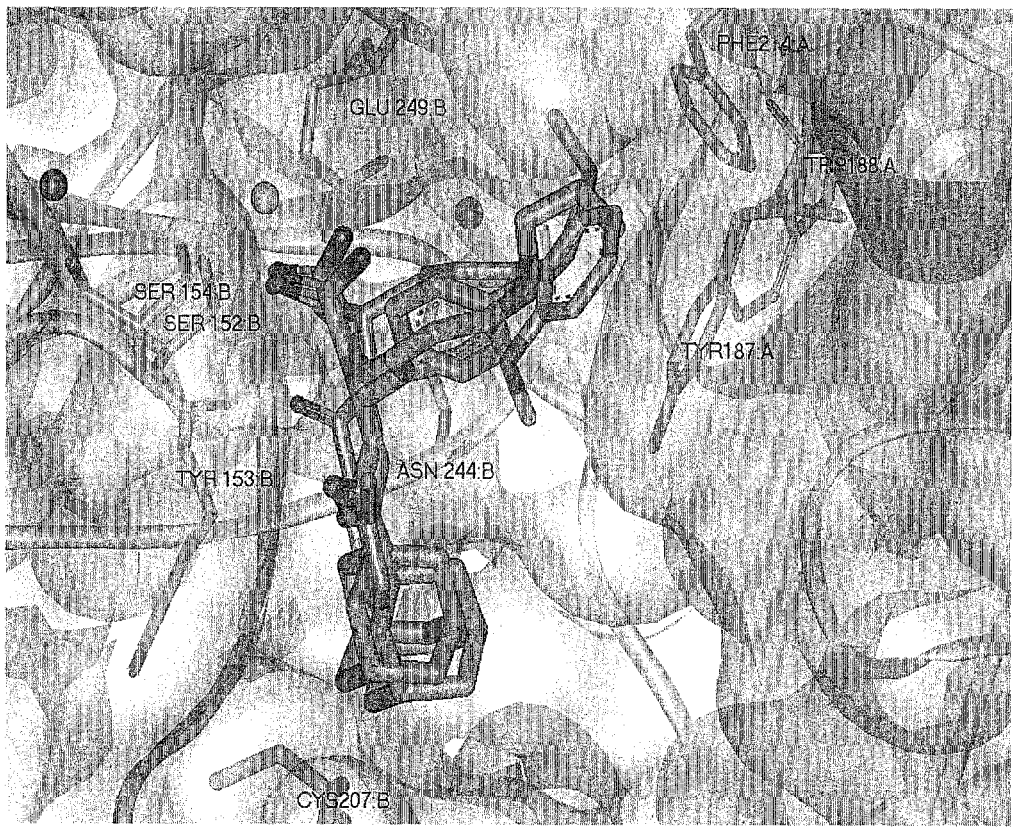
FIG. 7 shows the docking of compounds TR14035, D and E to a homology model for the headpiece of the VLA-4 integrin in the VLA-4 binding site.

Docking experiments were carried out with the compounds D, E and TR14035 as described in Methods to evaluate the modes of binding. The ligands share a similar trend in the docking model in that they interact with both integrin subunits, establishing hydrophobic interactions with aromatic residues from the beta-propeller (alpha subunit, FIG. 7, green surface) and hydrogen bonds with the I-like domain in the beta subunit (FIG. 7, gray surface). Also, in all docking models, the ligands' carboxylic acid groups form coordinate covalent bonds to the manganese ion of the MIDAS center (FIG. 7, green sphere). In the TR-14035-bound model, the 2,6-dimethoxy-biphenylic group is oriented toward the alpha subunit, being placed into a hydrophobic pocket defined by three aromatic residues: Phe214, Tyr187 and Trp188. The propoxy and ethoxy groups of the D and E compounds point to the same pocket, although in their case the hydrophobic interactions are not as strong as for TR-14035 compound. This is the only type of interaction observed between the ligands and the alpha subunit.

The fragment of the I-like domain embedded in the binding site contains mainly polar amino acids, thus a hydrogen bond network is observed in this area. The hydroxyl groups of the Ser152 and Ser154 side chains interact with carboxylic functions presented in all three ligands and form hydrogen bonds. An extra hydrogen bond is formed between the amidic moiety of compounds D and E and carbonylic group of Asn244 from the integrin backbone. In TR-14035 model, the amidic group is in a good orientation toward Asn244 but is located too far away from it for the interaction to be possible. The adamantyl substituents from the compounds D and E and the 2,6-dichlorobenzene ring from TR14035 are situated in a hydrophobic pocket close to the residues Tyr153 and Cys207. Another common interaction between VLA-4 and ligands is the coordination by carboxylic group of manganese ion of the MIDAS center. This coordination together with the hydrogen bonds helps to stabilize the ligand in the binding site.

Discussion

Integrins are a family of extracellular adhesion receptors that represents one of the modern therapeutic targets for multiple human diseases. In particular $\alpha_4$-integrins expressed on a variety of white blood cells are implicated in the pathogenesis of asthma, rheumatoid arthritis, inflammatory bowel diseases, and others. VLA-4/VCAM-1 interaction plays a role in the homing, retention, and mobilization of hematopoietic progenitors and stem cells in bone marrow. Vascular integrins play a role in tumor angiogenesis. Therefore, at least a dozen pharmaceutical companies are actively pursuing the development of $\alpha_4$-integrin ligands that block VCAM-1 binding but do not induce cell activation.

Previously, it has been reported that several different integrin ligands can "activate" integrin molecules. This activation is often described as "outside-in" signaling associated with integrin cross-linking after multivalent ligand binding. In a series of recent studies, binding of monovalent LDV containing ligands did not lead to time dependent affinity changes, even at saturating ligand concentrations. In contrast, cellular activation through G-protein coupled and several other receptors led to integrin affinity up-regulation. However, the exposure of HUTS-21 mAb epitope, used certain embodiments, can depend on ligand binding rather than cell activation. HUTS-21 binding can be detected in the presence of low ligand concentration for the high affinity state of the ligand binding pocket (activated integrin), or it required a higher ligand concentration for the low affinity state (i.e., the resting or inactive integrin conformation). "Inside-out" activation through G-protein coupled receptors had no direct effect upon HUTS epitope exposure. Thus, ligand binding by itself may mechanically induce a series of conformational changes, since ligand induced binding of HUTS-21 can be observed on ice. Thus, the exposure of the HUTS epitope appears to reflect a ligand induced binding site (LIBS).

Determination of Ligand Binding Affinity for the Unlabeled Ligand

Because the binding of our ligands to VLA-4 induces a conformational change, which can be detected using integrin specific antibodies, integrins represent a unique system where fractional occupancy of the ligand binding pocket can be assessed using conformationally sensitive mAbs. Moreover, this can be done using an unlabeled ligand, and thus, compounds can be tested over a wide range of concentrations. The other advantage is that because of antibody specificity the same compound can be used to study its binding to different integrins (as multiple integrins are reported to have shared ligands). Thus, this technology is ideal for use in a screen for novel compounds that have a quality that is unique for integrin ligands, namely to cause ligand induced conformational change. However, compounds that induce the conformational change may be considered agonists which have the potential to activate integrin signaling, and could exhibit less desirable side effects.

An alternative approach is a competition assay in which the unknown compound is competing against labeled ligand (fluorescent for the case of flow cytometry). In this case the major problem is that the affinity of the unlabeled compound in the primary screen is much lower than for the labeled ligand. Thus, a very high concentration of competitor is necessary. The other issue is ligand binding specificity. After the compound is identified, testing for binding specificity is required. This is not an issue in the case of conformationally sensitive mAb based assay which has a very high degree of binding specificity. Thus, the technology presented allows the detection of ligand binding in a simple and efficient way. In our hands, the sensitivity of mAb detection with phycoerythrin is nearly an order of magnitude better than direct detection of ligand binding with fluorescein. The dynamic range of the response spans ligands with affinity varying over all least three orders of magnitude.

Furthermore, the mAb method can be compatible with discrimination of ligands which induce the LIBS, as well as the detection of ligands, which compete and do not induce LIBS. The ability to detect ligand occupancy in a homogeneous assay without having to develop labeled ligand would facilitate primary and secondary screens for these novel ligands.

The results from these LIBS mAb binding studies provide further evidence that these VLA-4 ligands bind to the integrin's ligand binding pocket, thus directly competing with LDV-FITC rather than binding to an allosteric site. The docking studies suggest similar binding modes for the small molecules, although the increased affinity of TR14035 may results from its ability to interact with both integrin subunits.

Further Examples

Figure 8:
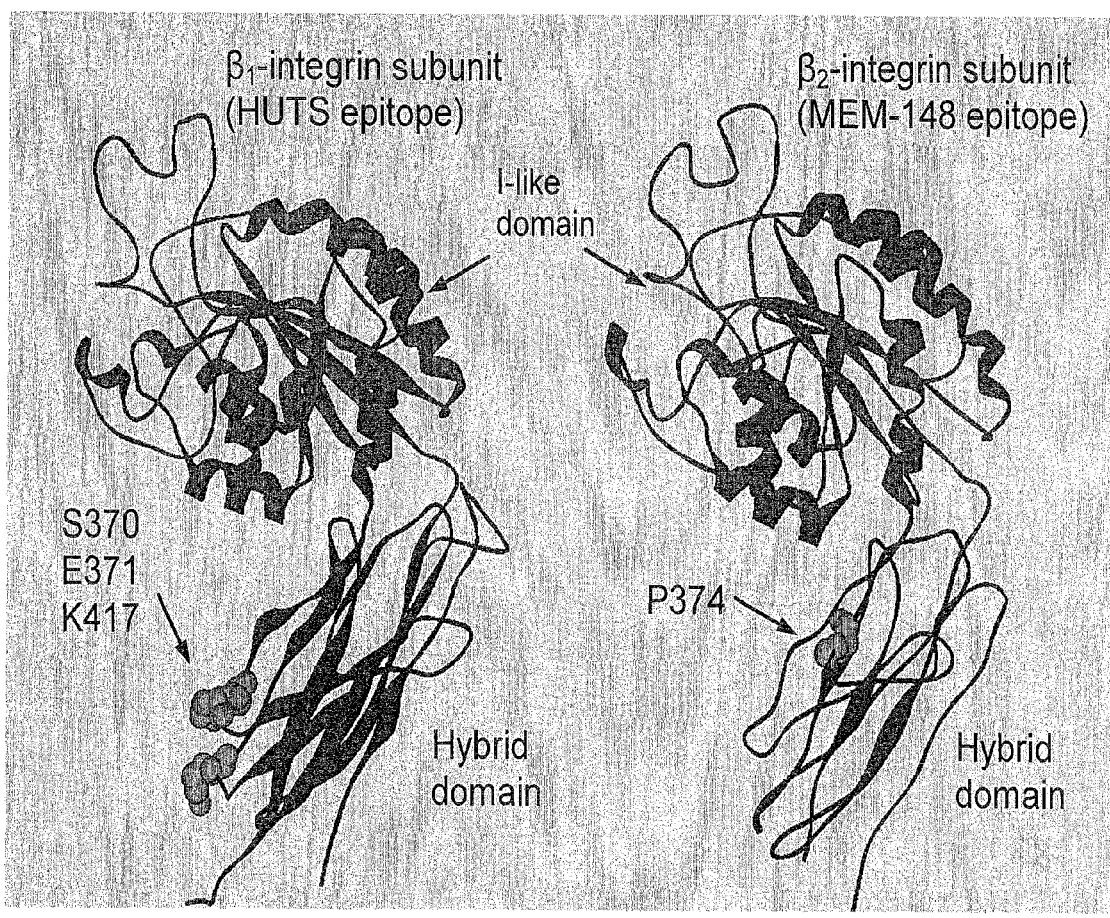
FIG. 8 shows localization of HUTS-21 and MEM-148 mAb epitopes in $\beta_1$-integrin subunit and $\beta_2$-integrin subunit respectively. Critical residues for mAb binding are indicated by light shaded space fill.

Exposure of $\beta_2$-Integrin Subunit Specific Epitopes in Response to Small Molecule LFA-1 Ligands Localization of $\beta_2$-Integrin Subunit Specific Epitopes In order to confirm that similar results can be obtained with other integrins we have constructed a 3D model of $\alpha_L\beta_2$-integrin (LFA-1, CD11a/CD18). Amino acid residue critical for the binding of MEM-148 mAb to $\beta_2$-integrin subunit (Pro 374) was highlighted as green space fill (1). This model was compared to the model of $\beta_1$-integrin subunit, where critical residues (Ser370, Glu371, and Lys417) were highlighted in a similar way (2) (FIG. 8). It is worth noting that critical residues for both mAbs are positioned in a similar way on the inner side of the hybrid domain. Since the outward movement of the hybrid domain, induced by a ligand binding (at least for $\beta_1$-integrin (2)), can be used to report occupancy of the ligand binding pocket (3), we decided to use MEM-148 mAbs to probe LFA-1 integrin conformation upon ligand binding.

LFA-1 Specific Ligands

Figure 9:
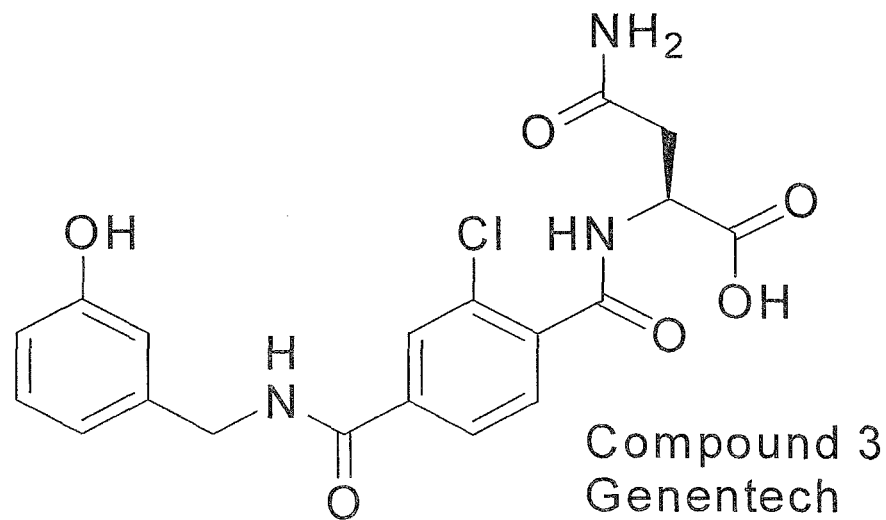
FIG. 9 shows LFA-1 specific ligands used in the experiments which are presented in the specification.
Figure 9:
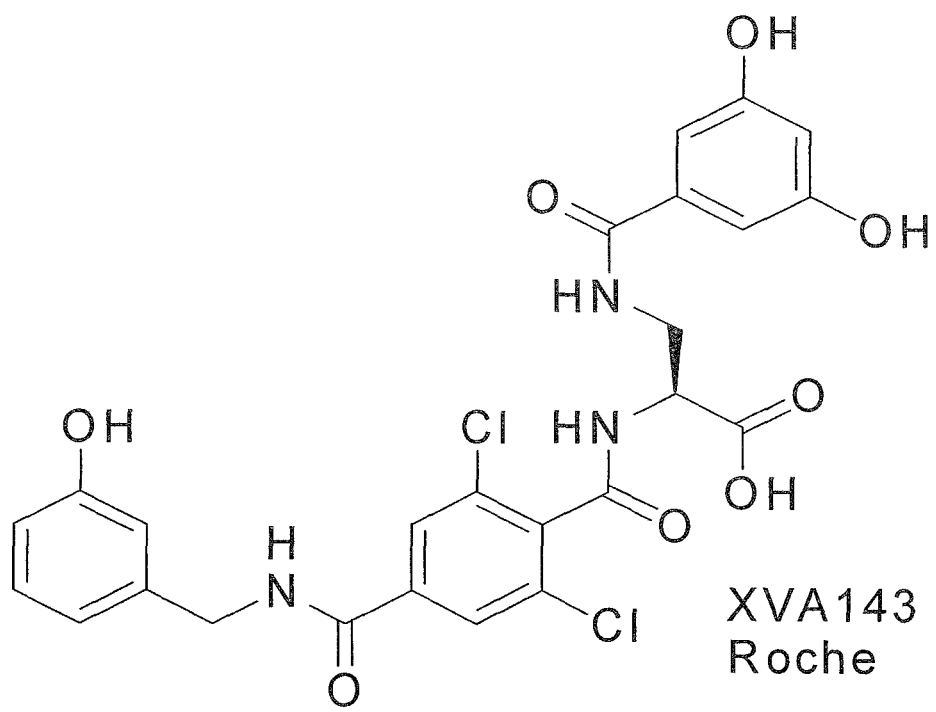

To test this possibility, two $\alpha_L\beta_2$-integrin ligands were synthesized as described previously. Compound 3 (Genentech) and XVA143 (Roche) are shown to be LFA-1 specific antagonists (4) FIG. 9.

Two LFA-1 Specific Ligand Induced MEM-148 Epitope Exposure

Figure 10:
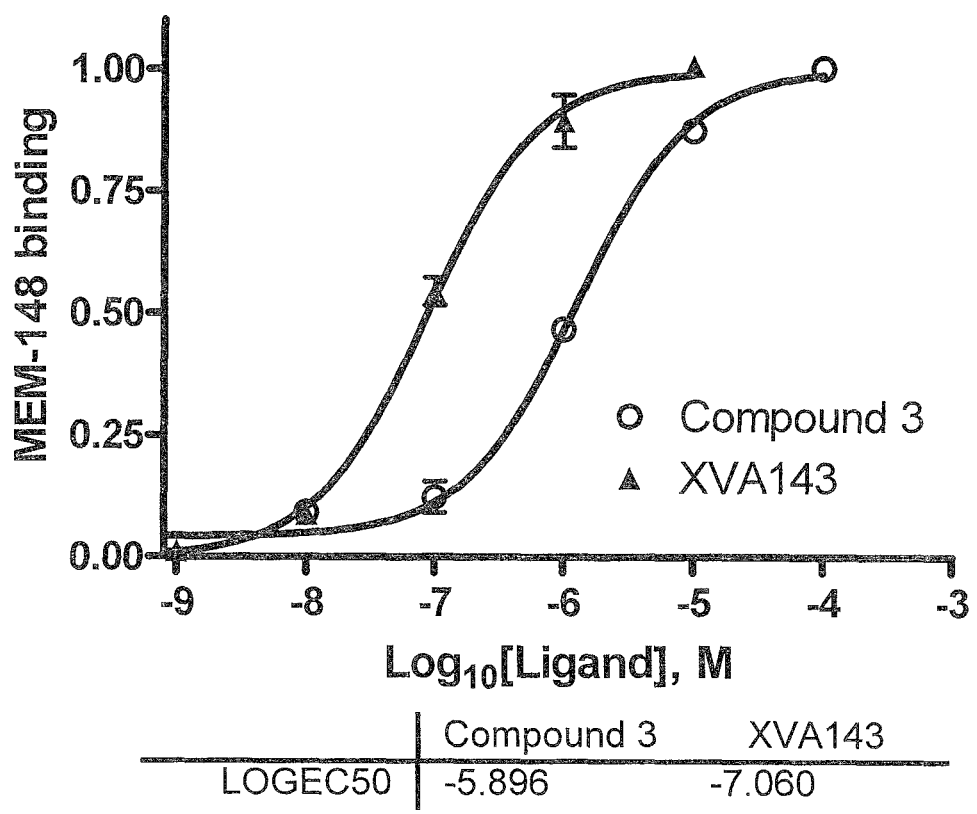
FIG. 10 shows the binding of MEM-148 mAbs to U937 cells in the presence of different concentrations of Compound 3 and XVA143. The two LFA-1 specific ligands induced exposure of MEM-148 epitope in a manner analogous to VLA-4 ligand and HUTS antobodies. Thus, the method for integrin ligand discovery can be generalized for use with different integrin molecules.

As expected two LEA-1 specific ligands induced exposure of MEM-148 epitope in a manner analogous to VLA-4 ligand and HUTS antobodies (FIG. 10). Thus, the method for integrin ligand discovery can be generalized for use with different integrin molecules.

Further Examples

In the following examples, reported is the identification of several structurally related compounds that were able to prevent exposure of ligand induced binding sites (LIBS) after the addition of VLA-4 specific ligand, decrease binding affinity of VLA-4 specific ligand, and block VLA-4/VCAM-1 dependent cell adhesion. Because these compounds are previously used or currently marketed drugs, which are known to possess immunosuppressive properties that are specifically attributed to the cell mediated component (4), this effect upon VLA-4 ligand binding provides a plausible explanation for the mechanism of immunosuppression. Note that the second set of references applies to the set of examples/experiments.

Experimental Procedures

Materials—

The VLA-4 specific ligand (22-24) 4-((N'-2-methylphenyl)ureido)-phenylacetyl-L-leucyl-L-aspartyl-L-valyl-L-prolyl-L-alanyl-L-alanyl-L-lysine (LDV), and its FITC-conjugated analog (LDV-FITC probe) were synthesized at Commonwealth Biotechnologies. Mouse anti-human CD29, HUTS-21(PE), isotype control (mouse IgG2a κ PE) clone G155-178 were purchased from BD Biosciences and used according to instructions of the manufacturer. Thioridazine hydrochloride and AMD3100 octahydrochloride (Plerixafor) were purchased from Tocris Bioscience, Ellisville, Mo. All other reagents were from Sigma-Aldrich. Small molecule stock solutions were prepared in DMSO, at concentrations ~1000 fold higher than the final concentration. Typically, 1 µl of stock solution was added to 1 ml cell suspension yielding a 0.1% final DMSO concentration. Control samples were treated with an equal amount of pure DMSO (vehicle).

Cells—

The mouse melanoma cell line B78H1 and the human histiocytic lymphoma cell line U937 were purchased from ATCC. Cells were grown at 37° C. in a humidified atmosphere of 5% $CO_2$ and 95% air in RPM 1640 (supplemented with 2 mM L-glutamine, 100 units/mL penicillin, 100 µg/mL streptomycin, 10 mM HEPES, pH 7.4, and 10% heat inactivated fetal bovine serum). Cells were then harvested and resuspended in 1 ml HEPES buffer (110 mM NaCl, 10 mM KCl, 10 mM glucose, 1 mM $MgCl_2$, 1.5 mM $CaCl_2$ and 30 mM HEPES, pH 7.4) containing 0.1% HSA and stored on ice. Cells were counted using the Coulter Multisizer/Z2 analyzer (Beckman Coulter). For experiments, cells were suspended in the same HEPES buffer at $10^6$ cells/ml and warmed to 37° C. for 10 min prior to binding experiments (see below).

For transfection of B78H1 cells, full-length human VCAM-1 cDNA was a kind gift from Dr. Roy Lobb of Biogen Inc. The original construct (25) was subcloned into the pTRACER vector (Invitrogen). Transfection was done using the LipofectAMINE Reagent (Invitrogen). High expressors were selected using the MoFlo Flow Cytometer (Cytomation, Inc., Fort Collins, Colo.).

Detection of VLA-4 Allosteric Antagonists—

HUTS-21 antibody binding has been thoroughly studied and described in detail (15; 16). Here we present the assay as adapted for small volumes (384 plate format) at the University of New Mexico Center for Molecular Discovery (UNM-CMD). The assay description was uploaded to PubChem (AIDs: 2617, 2674, 2813, 2557). 5 µl RPMI was added to columns 2-24. Column 1 was left empty for flow cytometry data binning purposes. Test compounds in DMSO (Prestwick Chemical Library, PCL) were added and mixed (0.1 µl of 1 mM stock solution). This resulted in 20 µM test compounds (6.7 µM final in 15 µl). Compounds were added to 320 wells (columns 3-22). Column 2 was used for the negative control (no VLA-4 ligand added). Columns 23, 24 were used for the positive control (no test compounds added). Next, 5 µl aliquots of U937 cells were suspended in RPMI 1640 at $3\times10^6$ cells/ml, loaded in 384 well plates, and mixed ($1\times10^6$ cells/ml final). Cells were incubated for 10 min at RT. This time is sufficient for the binding of a small molecule (~1 kD) at 10 µM at RT. Next, a 5 µl mixture of a non-fluorescent VLA-4 specific ligand (12 nM final) with HUTS-21 PE antibody (25 µl/ml final) was added to columns 3-24) and mixed. This concentration (12 nM) is equal to the dissociation constant of LDV ($K_d$). 5 µl aliquot of HUTS-21 (PE) antibody without LDV (25 µl/ml final) were added to a column 2, which was used as a negative control. Addition of LDV resulted in the HUTS-21 LIBS epitope exposure, and therefore initiated antibody binding. Plates were incubated for 1 hour at 37° C. According to the real-time kinetic studies this time was sufficient to reach equilibrium. Next, wells were sampled using the high throughput flow cytometry platform (HyperCyt) at UNMCMD.

After data acquisition by the flow cytometer (CyAn™ ADP), proprietary software was used to analyze the data files (IDLQuery, at UNMCMD, developed by Bruce Edwards). The data were exported into a Microsoft Excel spreadsheet template, and the value for antibody binding inhibition (%) was calculated for each well as follows: % Inhibition=100(1−(($MCF_{test}$−$MCF_{neg.control}$)/$MCF_{pos.control}$−$MCF_{neg.control}$))), where, MCF is mean channel fluorescence of cells with test compounds, and positive or negative control wells. A compound was considered a "hit" if the % inhibition was greater than 50%.

Real-Time Binding and Dissociation of VLA-4 Specific Ligand (LDV-FITC Probe)—

Kinetic analysis of the binding and dissociation of the LDV-FITC probe was described previously (22). Briefly, cells ($10^6$ cells/ml) were preincubated in HEPES buffer containing 0.1% HSA at different conditions for 10-20 min at 37° C. Alternatively, experiments were performed directly in RPMI that was used for growing the cells. Flow cytometric data were acquired for up to 1024 s at 37° C. while the samples were stirred continuously at 300 rpm with a 5×2 mm magnetic stir bar (Bel-Art Products). Samples were analyzed for 30-120 s to establish a baseline. The fluorescent ligand was added and acquisition was re-established, creating a 5-10 s gap in the time course.

For real-time inside-out integrin activation experiments, 4 nM LDV-FITC was added after establishing a baseline for unstained cells. Then, data were acquired for 2-3 minutes, and cells were activated with 100 nM fMLFF (high affinity FPR ligand). Acquisition was re-established, and data were acquired continuously for up to 1024 s. The concentration of the LDV-FITC probe used in the experiments (4 nM) was below the dissociation constant ($K_d$) for its binding to resting VLA-4 (low affinity state, $K_d$~12 nM), and above the $K_d$ for physiologically activated VLA-4 (high affinity state, $K_d$~1-2 nM) (22). Therefore, the transition from the low affinity to the high affinity receptor state led to increased binding of the probe (from ~25% to ~70-80% of receptor occupancy, as calculated based on the one site binding equation), which was detected as an increase in the mean channel fluorescence (MCF). Next, cells were treated with an excess unlabeled LDV containing small molecule (1 μM), or compounds of interest (10-30 μM) and the dissociation of the fluorescent molecule was followed.

For kinetic dissociation measurements without inside-out activation, cell samples were preincubated with the fluorescent probe (25 nM, ~2×$K_d$ (12 nM) for the resting state of VLA-4, 68% of receptor occupancy (22)), treated with excess unlabeled LDV containing small molecule (1 μM) or compounds of interest (10-30 μM) and the dissociation of the fluorescent molecule was followed. The resulting data were converted to MCF versus time using FCSQuery software developed by Dr. Bruce Edwards (University of New Mexico).

Real-Time Binding of HUTS-21 Antibodies— the Ability of a Flow Cytometer to Discriminate between free and bound fluorescent ligand in a homogeneous assay was used to determine the binding kinetics of mAbs in real-time (15; 26). Cells ($10^6$ cells/ml) were removed from ice and warmed in HEPES buffer containing 0.1% HSA for 10 min at 37° C. Flow cytometric data were acquired continuously for up to 2048 s at 37° C. while the samples were stirred continuously at 300 rpm with a 5×2 mm magnetic stir bar (Bel-Art Products). First, samples were analyzed for 30-120 s to establish a baseline. Next, the tube was removed and HUTS-21 mAbs (20 μl/1 ml of cells) were added and acquisition was re-established, creating a 5-10 s gap in the time course. In the absence of the LDV ligand no binding of HUTS-21 mAb were observed (15). Screening hits at saturating concentration (10-30 μM final) or DMSO (vehicle) were added at point 0. Next, different concentrations of LDV ligand were added after 60-120 s. Then, acquisition was re-established, and data were acquired continuously for up to 2048 s. The resulting data were converted to MCF versus time using FCSQuery software developed by Dr. Bruce Edwards (University of New Mexico).

Cell Adhesion Assay—

The cell suspension adhesion assay has been described previously (23; 27; 28). Briefly, U937 cells stably transfected with FPR were labeled with red fluorescent PKH26GL dye, and B78H1/VCAM-1 transfectants were stained with green fluorescent PKH67GL dye (Sigma-Aldrich). Labeled cells were washed, resuspended in HEPES buffer supplemented with 0.1% HSA or RPMI and stored on ice until used in assays. Control U937 cells were preincubated with the LDV-containing small molecule as a blocking agent. Prior to as data acquisition, cells were warmed to 37° C. for 10 min separately and then mixed. During data acquisition, the samples were stirred with a 5×2-mm magnetic stir bar (Bel-Art Products, Pequannock, N.J.) at 300 rpm and kept at 37° C. Next, cells were treated with different compounds (screening hits) or LDV (block). The number of cell aggregates containing U937 adherent to B78H1/VCAM-1 (red and green co-fluorescent particles) was followed in real-time. The percentage of aggregates was calculated as follows: %Agg=(number of aggregates/(number of aggregates+number of singlets))×100. Experiments were performed using a FACScan flow cytometer and Cell Quest software (Becton Dickinson, San Jose, Calif.). The data were converted to the number of aggregates versus time using FCSQuery software developed by Dr. Bruce Edwards (University of New Mexico).

Mice—

Male (57B16 mice (9-13 weeks) were purchased from Jackson Laboratories, Bar Harbor, Me. Mice were acclimated to the facility for at least one week on a 12 h light/dark cycle and standard diet. Experiments were conducted between 10:00 and 12:00 AM (lights on at 7:00 AM). Procedures used in this study were conducted by authorized personnel and approved by the Institutional Animal Care and Use Committee of University of New Mexico School of Medicine.

One hour prior to blood collection mice were injected intraperitoneally with vehicle, thioridazine hydrochloride (1.25 mg/kg), or AMD3100 octahydrochloride (Plerixafor, 5 mg/kg). Prior to blood collection mice were anaesthetized using isoflurane and monitored for sensitivity. Blood was collected by heart puncture and continued to exsanguination (1-1.4 ml). The blood was collected in a syringe containing heparin and immediately mixed into a heparin-containing tube to prevent clotting.

Hematopoietic Stem and Progenitor Cell (HSPC) Analysis—

Collected blood was processed according to the protocol recommended by Stemcell Technologies Inc. (http://www-.stemcell.com/en/Technical-Resources/Manuals.aspx).

Blood was lysed using ammonium chloride lysis buffer (StemCell Technologies Inc.). The cells were then washed with PBS, Iscove's modified Dulbecco medium supplemented with 2% FBS (IMDM), and re-suspended in IMDM supplemented with 2% FBS. An aliquot from each sample was resuspended in PBS and used for nucleated cell enumeration using a Vi-Cell automated cell counter (Becton Dickinson, San Jose, Calif.). To determine the white blood count (WBC, cell/ml), the total cell count was adjusted for the volume collected. Next, the samples were centrifuged, aspirated and re-suspended in IMDM-2% FCS to achieve $3×10^6$ cells/ml. The cells were counted again, and these cell counts were utilized as the established load count to determine colony-forming unit (CFU) values, CFU/ml. 300 μl of each load sample was added to a tube containing 3 ml of MethoCult media (MethoCult3534; StemCell Technologies), and mixed. 1.1 ml of the MethoCult media-cell mix was plated in pre-tested 35 mm culture dishes (two per sample) and incubated at 37° C., 5% $CO_2$. CFU values were counted 14 days later at 10× magnification.

Statistical Analysis—

Curve fits, statistics, and EC50 calculations were performed using GraphPad Prism version 4.00 for Windows, GraphPad Software, San Diego Calif. USA, www.graphpad.com. Each experiment was repeated at least two times. The experimental curves represent the mean of two or more independent determinations. The standard error of the mean was calculated using GraphPad Prism.

Results

Assay for the Detection of VLA-4 Allosteric Antagonists.

Recently, we studied the binding of the conformationally sensitive anti-CD29 antibody (HUTS-21). Our data indicate that intracellular signaling through G-protein coupled receptors (inside-out signal) does not affect the exposure of the HUTS-21 epitope mapped to the hybrid domain of the beta-1 integrin subunit. Exposure of this epitope is solely regulated by the occupancy of the ligand binding pocket, and is independent of integrin affinity state (14; 15). Moreover, exposure of the HUTS-21 epitope can be used to determine the affinity of unlabeled VLA-4 ligands. This was verified using competition between the LDV-FITC ligand and a number of VLA-4 specific ligands identified by us and others with affinities that differ by more than one order of magnitude (16).

To date, all of the competitive VLA-4 antagonists induced exposure of the HUTS-21 mAb epitope (16). Thus, the binding of anti-LIBS antibodies represents an ideal tool to study occupancy of the integrin binding pocket, and it provides a unique way to discriminate between competitive and allosteric antagonists. Allosteric antagonists, which bind to the allosteric sites of the molecule (by definition), would not induce ligand-induced conformational changes. However they would still block binding of the ligand. As a result, a direct competitor that induces the LIBS epitope would dissociate, and binding of anti-LIBS antibody would decrease. On the contrary, novel competitive ligands, in addition to blocking binding of the control ligand, have the potential to induce the LIBS epitope, and therefore would not be detected. Thus, this assay would specifically detect allosteric antagonists or non-canonical ligands (small molecules that bind to the ligand binding pocket without inducing LIBS epitope exposure).

HTS Screen Results.

The screen of the PCL was performed using the HyperCyt platform in 384 well plate format. The assay was configured to discriminate the non-specific binding of HUTS-21 as well as its specific binding to VLA-4 in the presence of LDV ligand. HUTS-21 binding in the presence of the compound of interest was calculated as % inhibition where the positive control is 100% and non-specific binding is 0.

Several chemical libraries have been screened using this specific screening assay. The results of primary and confirmatory assays were uploaded to the PubChem database (http://pubchem.nebi.nlm.nih.gov/, PubChem AIDs: 2557, 2617, 2674, 2813, 449766). Some of the identified compounds are found to be structurally similar to the compounds reported below (for example see "active" compounds in AID: 2674).

The screen identified 36 active molecules. About 31% of them belong to the same structural family, which consists of three different groups (phenothiazines, thioxanthenes, and structurally related 3-ring heterocyclic compounds). All of these compounds exhibit significant structural homology, and represent a single class of drugs that include serotonin-dopamine full and partial antagonists. These hits represent a series of compounds with inhibition ranging from 90% to 51%, which provide nascent SAR data. Here we present the data from secondary and tertiary assays for this dominant group of compounds.

Binding of the LDV-FITC Ligand.

The VLA-4 specific ligand (LDV-FITC) has been used extensively (22; 23; 29) as a tool for studying VLA-4 affinity and conformation. Here we probed whether hits from screening would interfere with the binding of this ligand. Cells were incubated with 25 nM LDV-FITC ($K_d$~12 nM) (22). Next, different concentrations of compound were added. As shown in FIG. 11A, addition of the compound resulted in the rapid dissociation of the LDV-FITC probe. The steady state value of LDV-FITC fluorescence (achieved about ~300 s after addition) plotted versus compound concentration is shown in FIG. 11B. EC50 values ranged from 3-13 μM. Thus, all five compounds interfered with the binding of the VLA-4 specific ligand to U937 cells at rest (without integrin activation).

VLA-4 can also be activated by cellular signaling. The "inside-out" signaling pathway can be triggered by G-protein coupled receptors. This results in a higher affinity of the ligand binding pocket. To study the effect of compound upon activated cells we used U937 cells stably transfected with a non-desensitizing mutant of the formyl peptide receptor (FPR). The major advantage of this mutant is that in the absence of receptor desensitization, the high affinity state of the VLA-4 binding pocket is preserved for several minutes after addition of its ligand (fMLFF) (24). Addition of compounds after cell activation by fMLFF resulted in the rapid dissociation of the LVD-FITC probe (FIG. 12A). In fact, the LDV-FITC "dissociation rate" was faster than after the addition of excess unlabelled competitor. This result suggests that none of the compounds competed directly with LDV-FITC, where the "dissociation rate" should equal the rate induced by a competitor. In this case the dissociation rate of the probe is determined by the life-time of the probe-receptor interaction and independent of the nature or affinity of a competitor (added in large excess). This suggests a non-competitive mechanism for the compounds.

Figure 12C:
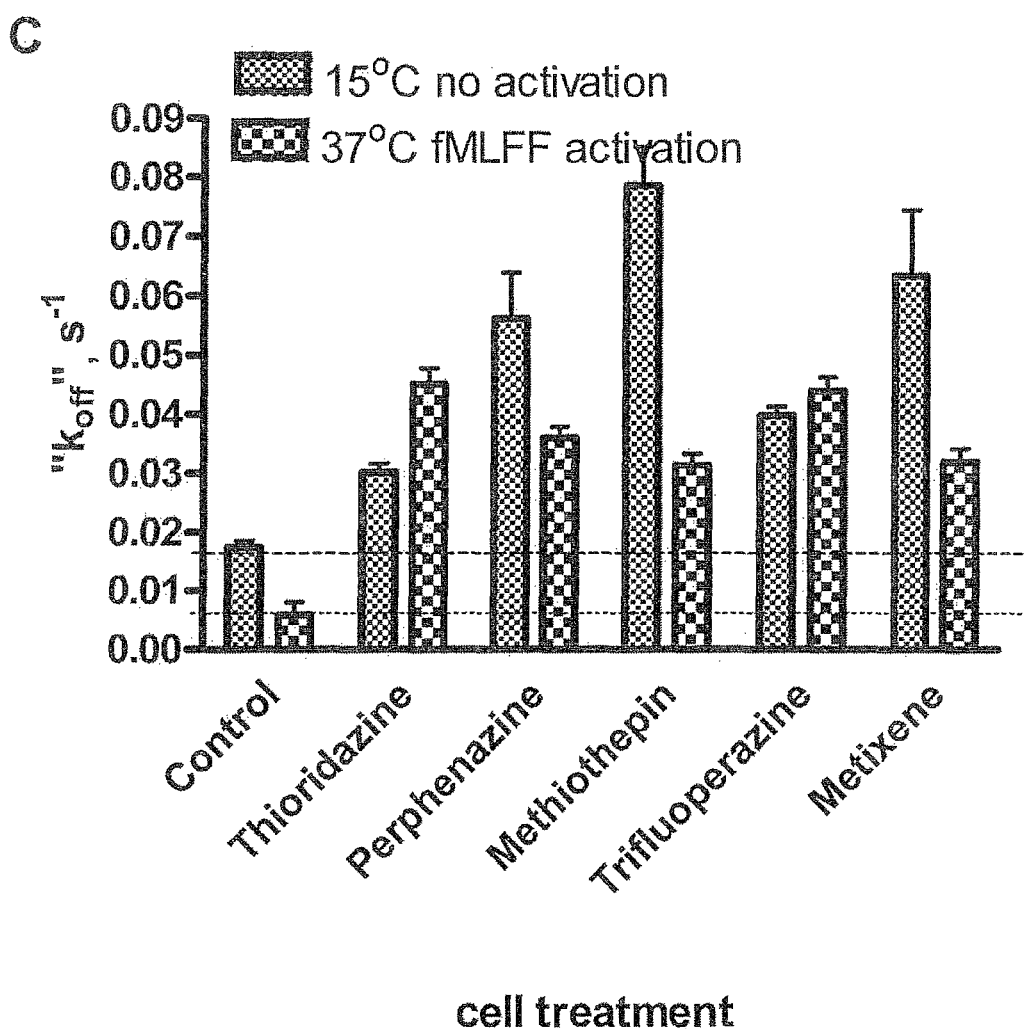
FIG. 12 shows the binding and dissociation of the LDV-FITC probe in response to the addition of screening hits. A, LDV-FITC probe binding and dissociation on U937 cells stably transfected with the non-desensitizing mutant of FPR plotted as mean channel fluorescence (FL1) versus time. The experiment involved sequential additions of fluorescent LDV-FITC probe (4 nM), fMLFF (100 nM), LDV (control, excess of unlabelled competitor), or saturating concentrations of compounds tested. One representative experiment (for trifluoperazine) out of two experiments for each compound is shown. B, LDV-FITC probe binding and dissociation on U937 cells plotted as mean channel fluorescence (FL1) versus time at low temperature (15° C.). The experiment involved sequential additions of fluorescent LDV-FITC probe (25 nM), LDV (control, excess of unlabelled competitor), or saturating concentration of compounds tested. One representative experiment (for trifluoperazine) out of two experiments for each compound is shown. C, LDV-FITC "dissociation rates" ("$k_{off}$") obtained in kinetic experiments analogous to the experiments shown in panels A and B. The dissociation parts of the curves were fitted to a single exponential equation using GraphPad Prism software and plotted for different compounds. Control represents actual dissociation rates obtained using an excess of unlabelled competitor (LDV). Notice that for all treatment conditions "$k_{off}$"s were larger than control, representing faster dissociation of the probe.

Recently, we described a signaling pathway that can actively down-regulate the affinity state of the ligand binding pocket (30). The PCL compounds could also be ligands for GPCRs that provide a signal for integrin de-activation. To study this question, we performed LDV-FITC binding experiments at low temperature (FIG. 12B). This allowed us to compare LDV-FITC dissociation rates without cell activation. At 15° C. without inside-out activation, the resting LDV-FITC dissociation rate was about 4 fold slower than at 37° C. Nonetheless, the rate of probe dissociation induced by all compounds was faster than for the LDV competitor (FIG. 12C). That the effect of compounds on LDV-FITC binding at 15° C. was as fast as at 37° C., suggests the lack of involvement of cellular signaling. The ability to down-regulate LDV-FITC binding at rest (without "inside-out" activation) further supports the absence of this type of signaling. The intracellular signaling, which triggers VLA-4 de-activation though the $G_\alpha s$-coupled pathway was only able to reduce VLA-4 affinity to the resting state, and not below that (30). Thus, all five studied compounds were able to decrease the binding of the LDV-FITC probe at low temperature, and without direct competition with the VLA-4 specific ligand.

Reversibility of Compound Binding.

Figure 13:
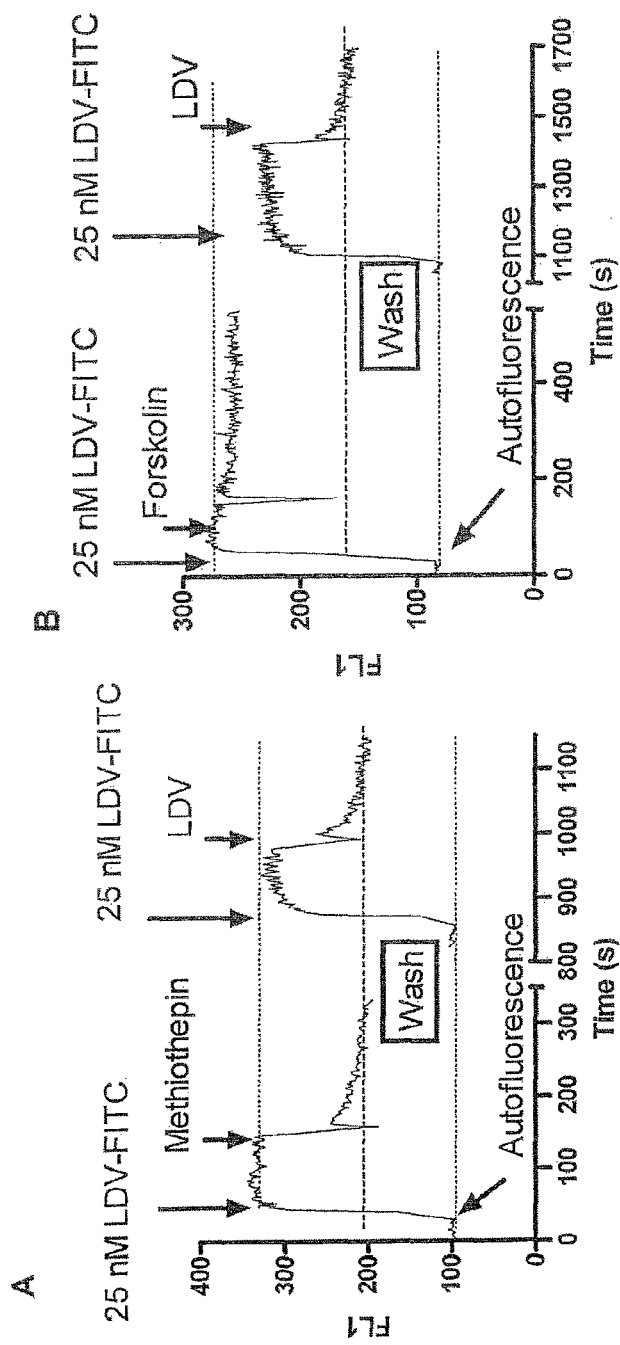
FIG. 13 shows the reversibility of compound binding assessed using binding and dissociation of the LDV-FITC probe in response to the addition of screening hits. A, LDV-FITC probe binding and dissociation on U937 cells plotted as mean channel fluorescence (FL1) versus time. The experiment involved sequential additions of fluorescent LDV-FITC probe (25 nM), and compounds tested (30 µM). After LDV-FITC probe dissociation the cells were washed three times in RPMI media to remove all traces of the compound. Next, binding of the LDV-FITC probe was repeated, followed by addition of the competitor (LDV). Notice that after the wash LDV-FITC binding was identical to the binding after first addition. This indicates that the compound blocking LDV-FITC binding after the first addition was completely removed by the wash. Thus, the binding of the compound was reversible. Analogous data were obtained for all five compounds tested (see FIG. 11 for the list). B, the same experiment as described in panel A using forskolin, activator of adenylyl cyclase. Notice slower effect after forskolin addition, and irreversible LDV-FITC blocking that involve intracellular signaling. Forskolin treatment is known to increase intracellular cAMP. This mimics activation of $G_\alpha$s-coupled GPCR signaling pathway.

To test the reversibility of compound binding, cells were consecutively treated with LDV-FITC and compounds of interest. Next, cells were washed three times with the media and LDV-FITC was added again. Excess LDV competitor was used to determine the non-specific binding of the compound (FIG. 13A). For all five studied compounds (see FIG. 11) the impact on LDV-FITC binding was fully reversible, indicating that no intracellular signaling was involved. As a control for the effect of the $G_\alpha s$-coupled signaling pathway, we used forskolin, which activates adenylyl cyclase, increases intacellular cAMP concentration, and is routinely used to mimic $G_\alpha s$-GPCR activation (30). As expected the impact of forskolin upon LDV-FITC binding was slow and irreversible (FIG. 13B). This further supports our notion that hits from screening do not cause $G_\alpha s$-GPCR activation.

Affinity of LDV Ligand Binding.

Figure 14:
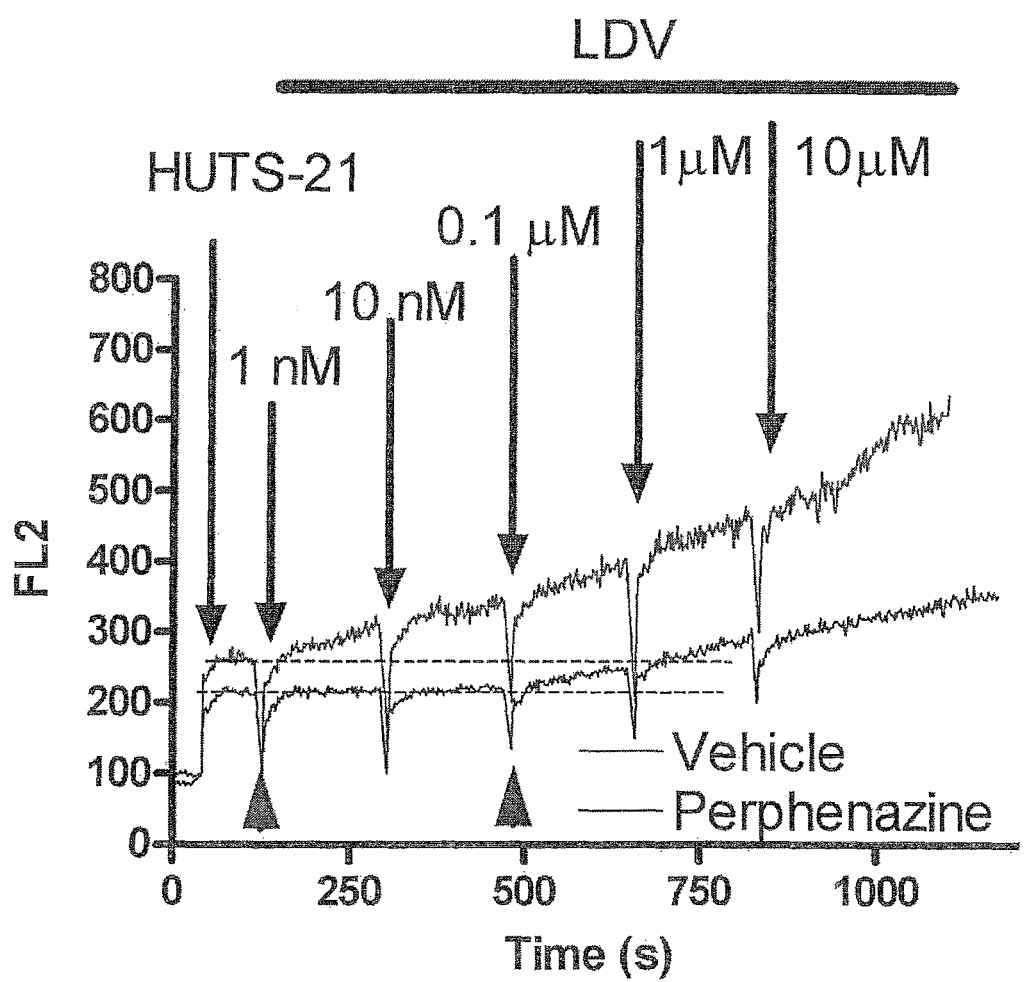
FIG. 14 shows the kinetics of real-time binding of HUTS-21 (PE) antibodies to U937 cells. Real-time binding of HUTS-21 antibodies plotted as mean channel fluorescence (FL2) versus time. Addition of HUTS-21 antibodies (first arrow) resulted in rapid non-specific binding of antibodies. Addition of increasing amounts of LDV ligand (arrows) resulted in the increased rates of antibody binding in the absence (red), or in the presence of the compound (blue). Compound was added at 0 time point. Notice that binding of HUTS-21 in the absence of the compound starts at 1 nM LDV (red arrowhead). To induce similar binding of HUTS-21 in the presence of the compound 0.1 µM of LDV was required (blue arrowhead). One representative experiment (for perphenazine) is shown. Analogous data were obtained for all five compounds tested (see FIG. 1 for the list).

Binding of the LDV-FITC probe can be studied in a homogeneous assay by flow cytometry, for concentrations up to 100 nM or more. At higher concentrations background fluorescence from the fluorescent probe in solution can dominate the analysis. To overcome this problem we developed an assay that relies on a real-time binding analysis of HUTS-21 mAbs in response to the addition of known amounts of unlabelled LDV probe (see FIG. 4A in ref. (15)). Because the HUTS-21 epitope is exposed as a result of ligand binding and the subsequent conformational change, this assay can be used to evaluate how the presence of a hit compound affects the ligand binding affinity at high ligand concentrations (FIG. 14). HUTS-21 binding was detected following the addition of 1 nM LDV in the absence of the compound (red line/arrowhead). In the presence of the compound HUTS-21 binding was detected at a concentration~two orders of magnitude higher (blue arrowhead, 0.1 μM). This suggests that the ligand binding affinity was lowered by a factor of 100. These data support previous real-time LDV-FITC binding results. Lowering ligand affinity by about 100 fold produces the dramatic dissociation of the LDV-FITC probe shown in FIGS. 12 and 13. This represents a transition at 4 nM ($K_d$~2 nM: FPR activated state) from ~67% receptor occupancy to ~2% occupancy (FIG. 12), or a transition at 25 nM ($K_d$~12 nM: resting state) from ~68% receptor occupancy to ~2% occupancy (FIG. 13A) respectively.

Cell Aggregation.

Figure 15:
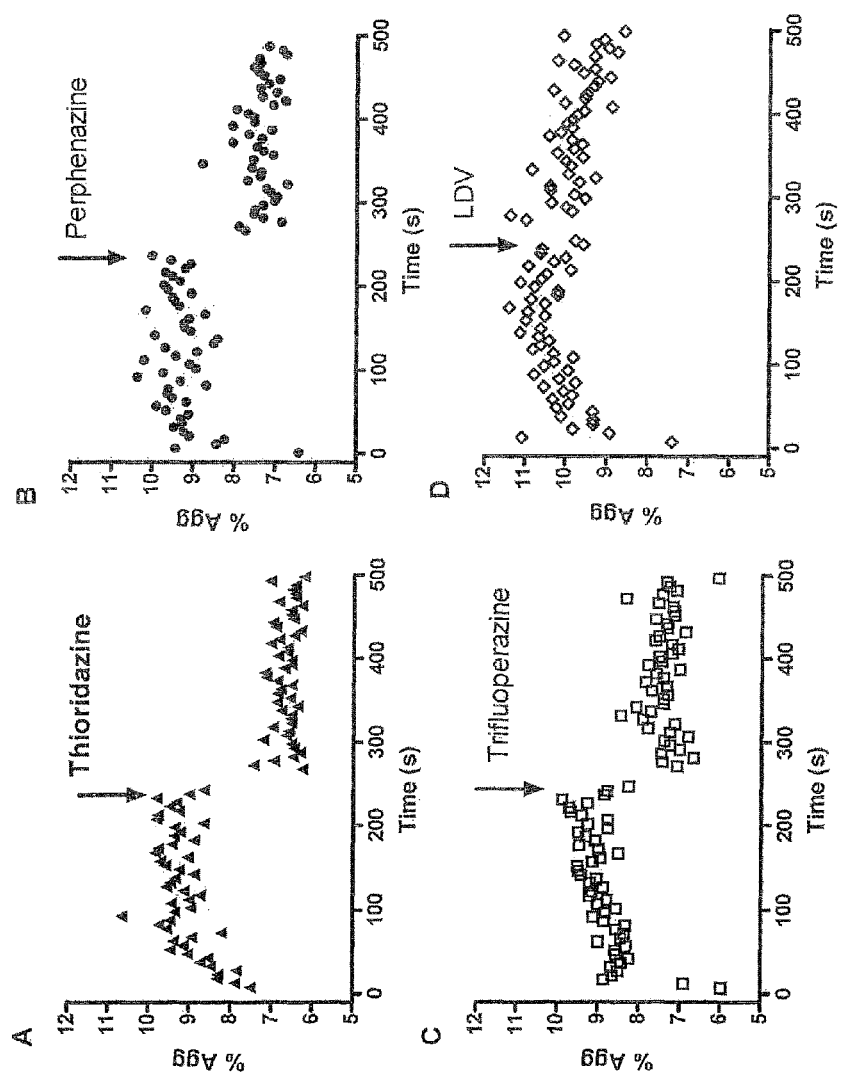
FIG. 15 shows the changes in cell adhesion between VLA-4 expressing U937 cells and VCAM-1-transfected B78H1 cells in response to compounds addition. U937 cells were stained using red fluorescent dye (PKH26), and B78H1/VCAM-1 cells were stained using green fluorescent dye (PKI167). Cells were mixed at 37° C. and sampled continuously using a flow cytometer. Double positive (red and green) cell aggregates were followed as described in Experimental Procedures, and plotted as % of aggregates (% Agg) versus time. 30 µM of individual compounds (A, B, and C) or 1 µM of LDV competitor were added. Notice the rapid decrease in number of cell aggregates after the addition of allosteric antagonists. Representative experiment out of two experiments is shown.

To study the effect of screening hits on VLA-4 dependent cell adhesion, we used a well-characterized cell suspension adhesion assay (24; 27; 28). U937 cells expressing VLA-4 and B78H1 mouse melanoma cells stably transfected with human VCAM-1 (stained with red and green dyes) form VLA-4/VCAM-1 dependent cellular aggregates after mixing. Cell aggregation was followed in real-time. Addition of saturating amounts of screening hits resulted in rapid cellular disaggregation (FIG. 15). Moreover, this disaggregation was much faster than disaggregation induced by LDV (FIG. 15D). The rate of cell disaggregation depends upon the life-time of the VLA-4/VCAM-1 "bond", which is determined by the affinity state of the VLA-4 binding pocket, and the number of "bonds" (23; 27). Rapid disruption of cell aggregates is consistent with reduction of the bond life-time, caused by lowering the ligand-receptor affinity (as detected in the LDV probe binding assays, see above). The fact that a direct competitor (LDV) induces cellular disaggregation at a slower rate further supports this idea.

Mobilization of Hematopoietic Stem and Progenitor Cells (HSPCs) into the Peripheral Blood—

VLA-4 plays a specific role in the retention, homing, and engraftment of HSPCs (1; 2). It is expressed on human CD34+ cells, and murine HSPCs (31-33). Blocking the interaction between VLA-4 and its ligands using anti-VLA-4 specific antibodies, or small molecule inhibitors induces mobilization of HSPCs in humans (34; 35), primates (36; 37), and mice (38). Moreover, VLA-4 blockade alone, without additional cytokine treatment, is sufficient to induce HSPC mobilization (see (37) and references therein). Blockade of other leukocyte integrins, such as $\beta_2$-integrins using anti-CD18 antibodies, has no effect on progenitor mobilization (36). Thus, the effect of different VLA-4 antagonists on hematopoietic progenitor mobilization is highly VLA-4 specific, and these molecules alone can be used to induce HSPC mobilization.

Figure 11:
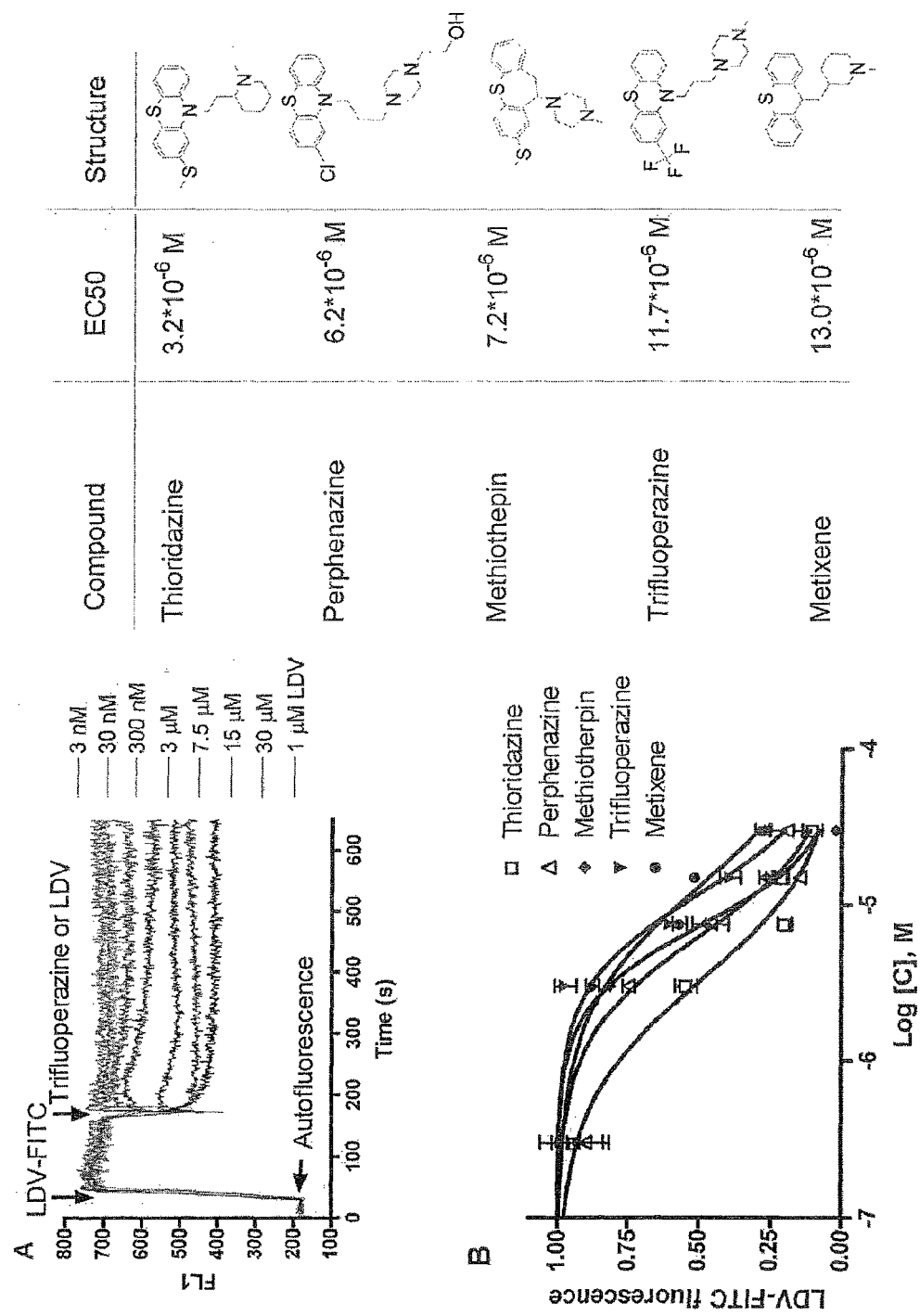
FIG. 11 shows the binding and dissociation of the LDV-FITC probe in response to the addition of screening hits. A, LDV-FITC probe binding and dissociation on U937 cells plotted as mean channel fluorescence (FL1) versus time. The experiment involved sequential additions of fluorescent LDV-FITC probe (25 nM), LDV (1 µM, control, excess of unlabelled competitor), or different concentrations of compounds tested. One representative experiment out of two experiments for each compound is shown. B, The steady state value of the LDV-FITC fluorescence obtained in the experiments analogous to the one shown in panel A 300-400 seconds after compound addition plotted versus compound concentration. LDV-FITC fluorescence was normalized assuming that the value of fluorescence after LDV addition is equal to 0, and after DMSO addition (vehicle) is equal to 1. The data represent means±SEM (n=2) for two independent experiments. Curves represent a fit to a sigmoidal dose response equation (variable slope) performed using GraphPad Prism software. EC50s and compound structures are shown one the right.

As compounds of interest (FIG. 11) exhibit properties of VLA-4 antagonists in vitro, we hypothesized that they will also act in vivo in a manner similar to other VLA-4 antagonists, which induce HSPC mobilization. To test this hypothesis, mice were injected with thioridazine, the most potent compound in the series (FIG. 11). As a control, we used the highly selective CXCR4 chemokine receptor antagonist AMD3100 (Plerixafor), which is known to stimulate a rapid increase in the number of circulating HSPC in mice and man (39-41).

We found that administration of thioridazine resulted in a significant increase in the number of CFUs in the peripheral blood (Table 2, below). The cell mobilizing ability of thioridazine was comparable to AMD3100. However, we also found a significant difference between the two treatments in the ability to modulate WBC. Thioridazine had no effect on WBCs, while AMD3100 significantly increased the WBC count. These data are in agreement with previously published reports. Blockade of VLA-4 using anti-VLA-4 antibodies mobilized hematopoietic progenitors without a significant increase in circulating white cells (36). AMD3100 is shown to induce an increase in the WBC count ranging from 1.5 to 3.1 times the baseline (42). In our experiments we observed ~2.1 fold WBC count increase. Thus, administration of thioridazine induced mobilization of HSPCs into the peripheral blood in mice. This data supports the idea that the identified compounds possess the properties of VLA-4 antagonists.

TABLE 2

Effect of intraperitoneal administration of thioridazine and AMD3100 upon CFU and WBC in mouse peripheral blood
Mean ± S.E. from three independent experiments performed on different days are shown (4 mice per treatment).

| Treatment | CFU/ml in peripheral Blood | WBC count/ml × $10^6$ |
|---|---|---|
| Vehicle | 68.1 ± 9.1 | 3.7 ± 0.6 |
| Thioridazine | 216.8 ± 42.1 | 3.0 ± 0.3 |
| AMD3100 | 511.8 ± 78.8[a] | 7.8 ± 0.7[b] |

[a]Means are significantly different (p < 0.05, according to one-way ANOVA).
[b]Statistically significant difference was found between vehicle and AMD3100 treatment (p < 0.05, according to unpaired t test). No significant difference was found between vehicle and thioridazine treatment for WBC count.

Taken together the experimental data presented herein suggest that all five compounds of interest (thioridazine, perphenazine, methiothepin, trifluoperazine, metixene) exhibit properties of VLA-4 specific allosteric antagonists. Since all these compounds are structurally related FDA approved drugs, these compounds may be used for the treatment of VLA-4-dependent diseases.

Discussion

A number of neuroleptic compounds are known to downmodulate the immune response. One of the earliest reports showed that neuroleptic drugs, structurally similar to the compounds tested in the present study, were able to protect mice receiving fatal doses of a bacterial endotoxin (43). Recent reports showed that the use of typical antipsychotic drugs was associated with a dose-dependent increase in the risk for pneumonia in elderly patients (44). However, the most remarkable finding is that the immunosuppressive effect of these drugs is not related to their dopamine antagonistic properties. More specific dopamine antagonists, which are based on an entirely different structural scaffold (such as haloperidol, metoclopramide, or sulpiride), do not possess any immuno-suppressive properties (20). These drugs were also present in the Prestwick Chemical Library, and they did not show any antagonistic activity in the HUTS-21 based screen to detect VLA-4 allosteric antagonists. Moreover, the structure-activity relationship of phenothiazines for inhibiting lymphocyte motility, is reported to be different from those for their neuroleptic effects (45). Thus, it is possible that some of the structural features of these compounds are specific for VLA-4 antagonistic properties. This indicates the possibility to develop VLA-4 allosteric antagonists that lack unwanted activity (such as dopamine receptor antagonism or others).

The immunological mechanism of neuroleptic drug-induced immunosuppression is not fully understood, and the modulation of cytokine production or cytokine networks could be an underlying mechanism (46). Our finding that these drugs exhibit properties of VLA-4 allosteric antagonists provides an excellent explanation for such activity. Other VLA-4 specific competitive antagonists in some cases can cause severe immune suppression (47), and increase the risk of opportunistic infections (48). Blocking VLA-4-dependent immune cell adhesion could also explain why these types of compounds selectively affect cell-mediated component of the immune function (20).

One report linked the use of phenothiazines and the appearance of "atypical lymphocytes" in the peripheral blood of schizophrenic and nonschizophrenic patients. Some of these cells morphologically resembled early hematopoietic progenitors (49). This may account for our observation that thioridazine, a widely used phenothiazine, mobilized hematopoietic progenitors into the peripheral blood.

Finally, allosteric antagonists that modulate the binding affinity of natural ligands are envisioned as a potent novel generation of antagonists, with somewhat greater therapeutic potential than competitive antagonists. In some cases this modulation can simply mimic the effects of competitive antagonists (50) (at least for G-protein coupled receptors). For integrins, which can propagate signals in both directions (inside-out and outside-in) (51), allosteric antagonists would lack the ability to induce an outside-in signal, or at least block natural ligand binding without inducing the ligand-induced binding site (LIBS) epitope.

Abbreviations

The following abbreviations were used to describe components or other chemicals used in conducting experiments, described above.

cAMP (adenosine 3',5'-cyclophosphate), fMLFF (N-formyl-L-methionyl-L-leucyl-L-phenylalanyl-L-phenylalanine, formyl peptide), FPR (formyl peptide receptor 1), GPCR (guanine nucleotide binding protein coupled receptor), HSA (human serum albumin), HTS (high throughput screen), HEPES (4-(2-hydroxyethyl)-1-piperazineethanesulfonic acid), LDV containing small molecule (4-((N'-2-methylphenyl)ureido)-phenylacetyl-L-leucyl-L-aspartyl-L-valyl-L-prolyl-L-alanyl-L-alanyl-L-lysine), LDV-FITC containing small molecule (4-((N'-2-methylphenyl)ureido)-phenylacetyl-L-leucyl-L-aspartyl-L-valyl-L-prolyl-L-alanyl-L-alanyl-L-lysine-FITC), mAb (monoclonal antibody) LFA-1 (lymphocyte function-associated antigen-1, CD11a/CD18, $\alpha_L\beta_2$ integrin), MCF (mean channel fluorescence, equivalent of mean fluorescence intensity), PCL (Prestwick Chemical Library), VCAM-1 (vascular cell adhesion molecule 1, CD106), VLA-4 (very late antigen 4, CD49d/CD29, $\alpha_4\beta_1$ integrin).

It is noted that, as used in this specification and the appended claims, the singular forms "a," "an," and "the," include plural referents unless expressly and unequivocally limited to one referent. Thus, for example, reference to "a epitope" includes two or more different epitopes. As used herein, the term "include" and its grammatical variants are intended to be non-limiting, such that recitation of items in a list is not to the exclusion of other like items that can be substituted or other items that can be added to the listed items.

Upon studying the disclosure, it will be apparent to those skilled in the art that various modifications and variations can be made in the devices and methods of various embodiments of the invention. Other embodiments will be apparent to those skilled in the art from consideration of the specification and practice of the embodiments disclosed herein. It is intended that the specification and examples be considered as examples only. The various embodiments are not necessarily mutually exclusive, as some embodiments can be combined with one or more other embodiments to form new embodiments.

REFERENCES

First Set

1. Tang, R. H., Tng, E., Law, S. K., and Tan, S. M. (2005) *J. Biol. Chem.* 280, 29208-29216
2. Mould, A. P., Barton, S. J., Askari, J. A., McEwan, P. A., Buckley, P. A., Craig, S. E., and Humphries, M. J. (2003) *J. Biol. Chem.* 278, 17028-17035
3. Chigaev, A., Waller, A., Amit, O., Halip, L., Bologa, C. G., and Sklar, L. A. (2009) *J. Biol. Chem.* 284, 14337-14346
4. Shimaoka, M. and Springer, T. A. (2003) *Nat. Rev. Drug Discov.* 2, 703-716

REFERENCES

Second Set

1. Lapidot, T. and Petit, I. (2002) *Exp. Hematol.* 30, 973-981
2. Lapidot, T., Dar, A., and Kollet, O. (2005) *Blood* 106, 1901-1910
3. Johnson, J. P. (1999) *Cancer Metastasis Rev.* 18, 345-357
4. Yoneda, T. (2000) *J. Orthop. Sci.* 5, 75-81
5. Yusuf-Makagiansar, H., Anderson, M. E., Yakovleva, T. V., Murray, J. S., and Siahaan, T. J. (2002) *Med. Res. Rev.* 22, 146-167
6. Jackson, D. Y. (2002) *Curr. Pharm. Des* 8, 1229-1253
7. Schmidmaier, R. and Baumann, P. (2008) *Curr. Med. Chem.* 15, 978-990
8. Dijkgraaf, I., Beer, A. J., and Wester, H. J. (2009) *Front Biosci.* 14, 887-899
9. Humphries, M. J. (2004) *Biochem. Soc. Trans.* 32, 407-411
10. Shimaoka, M. and Springer, T. A. (2003) *Nat. Rev. Drug Discov.* 2, 703-716
11. Woodside, D. G. and Vanderslice, P. (2008) *BioDrugs.* 22, 85-100
12. Frelinger, A. L., III, Du, X. P., Plow, E. F., and Ginsberg, M. H. (1991) *J. Biol. Chem.* 266, 17106-17111
13. Frelinger, A. L., III, Cohen, I., Plow, E. F., Smith, M. A., Roberts, J., Lam, S. C., and Ginsberg, M. H. (1990) *J. Biol. Chem.* 265, 6346-6352
14. Mould, A. P., Barton, S. J., Askari, J. A., McEwan, P. A., Buckley, P. A., Craig, S. E., and Humphries, M. J. (2003) *J. Biol. Chem.* 278, 17028-17035
15. Chigaev, A., Waller, A., Amit, O., Halip, L., Bologa, C. G., and Sklar, L. A. (2009) *J. Biol. Chem.* 284, 14337-14346

16. Njus, B. H., Chigaev, A., Waller, A., Wlodek, D., Ostopovici-Halip, L., Ursu, O., Wang, W., Oprea, T. I., Bologa, C. G., and Sklar, L. A. (2009) *Assay. Drug Dev. Technol.* 7, 507-515
17. Sudeshna, G. and Parimal, K. (2010) *Eur. J. Pharmacol.* 648, 6-14
18. Shen, W. W. (1999) *Compr. Psychiatry* 40, 407-414
19. Thanacoody, H. K. (2007) *Br. J. Clin. Pharmacol.* 64, 566-574
20. Roudebush, R. E., Berry, P. L., Layman, N. K., Butler, L. D., and Bryant, H. U. (1991) *Int. J. Immunopharmacol.* 13, 961-968
21. Surman, O. S. (1993) *Psychosomatics* 34, 139-143
22. Chigaev, A., Blenc, A. M., Braaten, J. V., Kumaraswamy, N., Kepley, C. L., Andrews, R. P., Oliver, J. M., Edwards, B. S., Prossnitz, E. R., Larson, R. S., and Sklar, L. A. (2001) *J. Biol. Chem.* 276, 48670-48678
23. Chigaev, A., Zwartz, G., Graves, S. W., Dwyer, D. C., Tsuji, H., Foutz, T. D., Edwards, B. S., Prossnitz, E. R., Larson, R. S., and Sklar, L. A. (2003) *J. Biol. Chem.* 278, 38174-38182
24. Chigaev, A., Buranda, T., Dwyer, D. C., Prossnitz, E. R., and Sklar, L. A. (2003) *Biophys. J.* 85, 3951-3962
25. Osborn, L., Hession, C., Tizard, R., Vassalo, C., Luhowskyj, S., Chi-Rosso, G., and Lobb, R. (1989) *Cell* 59, 1203-1211
26. Sklar, L. A., Edwards, B. S., Graves, S. W., Nolan, J. P., and Prossnitz, E. R. (2002) *Annu. Rev. Biophys. Biomol. Struct.* 31, 97-119
27. Zwartz, G., Chigaev, A., Foutz, T., Larson, R. S., Posner, R., and Sklar, L. A. (2004) *Biophys. J.* 86, 1243-1252
28. Edwards, B. S., Curry, M. S., Tsuji, H., Brown, D., Larson, R. S., and Sklar, L. A. (2000) *J. Immunol.* 165, 404-410
29. Chigaev, A., Waller, A., Zwartz, G. J., Buranda, T., and Sklar, L. A. (2007) *J. Immunol.* 178, 6828-6839
30. Chigaev, A., Waller, A., Amit, O., and Sklar, L. A. (2008) *BMC. Immunol.* 9, 26
31. Gazitt, Y. (2004) *Leukemia* 18, 1-10
32. Oostendorp, R. A. and Dormer, P. (1997) *Leuk. Lymphoma* 24, 423-435
33. Coulombel, L., Auffray, I., Gaugler, M. H., and Rosemblatt, M. (1997) *Acta Haematol.* 97, 13-21
34. Bonig, H., Wundes, A., Chang, K. H., Lucas, S., and Papayannopoulou, T. (2008) *Blood* 111, 3439-3441
35. Zohren, F., Toutzaris, D., Klarner, V., Hartung, H. P., Kieseier, B., and Haas, R. (2008) *Blood* 111, 3893-3895
36. Papayannopoulou, T. and Nakamoto, B. (1993) *Proc. Natl. Acad. Sci. U.S.A* 90, 9374-9378
37. Bonig, H., Watts, K. L., Chang, K. H., Kiem, H. P., and Papayannopoulou, T. (2009) *Stem Cells* 27, 836-837
38. Ramirez, P., Rettig, M. P., Uy, G. L., Deych, S. Holt, M. S., Ritchey, J. K., and DiPersio, J. F. (2009) *Blood* 114, 1340-1343
39. Broxmeyer, H. E., Orschell, C. M., Clapp, D. W., Hangoc, G., Cooper, S., Plett, P. A., Liles, W. C., Li, X., Graham-Evans, B., Campbell, T. B., Calandra, G., Bridger, G., Dale, D. C., and Srour, E. F. (2005) *J. Exp. Med* 201, 1307-1318
40. Hatse, S., Princen, K., Bridger, G., De Clercq, E., and Schols, D. (2002) *FEBS Lett.* 527, 255-262
41. Liles, W. C., Broxmeyer, H. E., Rodger, E., Wood, B., Hubel, K., Cooper, S., Hangoc, G., Bridger, G. J., Henson, G. W., Calandra, G., and Dale, D. C. (2003) *Blood* 102, 2728-2730
42. Hendrix, C. W., Flexner, C., MacFarland, R. T., Giandomenico, C., Fuchs, E. J., Redpath, E., Bridger, G., and Henson, G. W. (2000) *Antimicrob. Agents Chemother.* 44, 1667-1673
43. CHEDID, L. (1954) *C. R. Seances Soc. Biol. Fil.* 148, 1039-1043
44. Trifiro, G., Gambassi, G., Sen, E. F., Caputi, A. P., Bagnardi, V., Brea, J., and Sturkenboom, M. C. (2010) *Ann. Intern. Med.* 152, 418-440
45. Matthews, N., Franklin, R. J., and Kendrick, D. A. (1995) *Biochem. Pharmacol.* 50, 1053-1061
46. Pollmacher, T., Haack, M., Schuld, A., Kraus, T., and Hinze-Selch, D. (2000) *J. Psychiatr. Res.* 34, 369-382
47. Berger, J. R. and Houff, S. (2006) *Neurol. Res.* 28, 299-305
48. Rigal, E., Gateault, P., Lebranchu, Y., and Hoarau, C. (2009) *Med. Sci.* (Paris) 25, 1135-1140
49. Fieve, R. R., Blumenthal, B., and Little, B. (1966) *Arch. Gen. Psychiatry* 15, 529-534
50. Kenakin, T. (2004) *Mol. Interv.* 4, 222-229
51. Arnaout, M. A., Mahalingam, B., and Xiong, J. P. (2005) *Annu. Rev. Cell Dev. Biol.* 21, 381-410

---

What is claimed is:

1. A method for determining whether or not a compound of unknown integrin activity is an allosteric inhibitor of an integrin molecule selected from the group consisting of Very Late Antigen 4 (VLA-4, CD49d/CD29) and Leukocyte Function-Associated Antigen (LFA-1, CD18/CD11a) comprising exposing said integrin molecule to a known competitive ligand of said integrin molecule in the presence of an integrin-epitope binding antibody comprising a reporter moiety, measuring the binding of said antibody to the integrin molecule in the presence of the competitive ligand; thereafter exposing said bound integrin molecule in the presence of known competitive ligand and bound antibody to a compound of unknown activity and measuring the binding of the antibody to the integrin molecule, wherein the decrease in binding of antibody to integrin is evidence that the compound of unknown activity is an allosteric inhibitor of integrin, wherein said binding antibody for said VLA-4 integrin molecule is monoclonal antibody clone HUTS-21, said binding antibody for said LFA-1 integrin molecule is monoclonal antibody clone MEM-148, said competitive ligand of said VLA-4 integrin molecule is a compound according to the chemical structure:

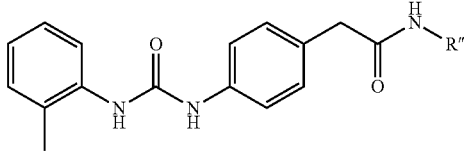

where R" is a peptide of SEQ ID NO:1 (compound LDV) or SEQ ID NO:2 (compound YLDV), N-(2,6-dichlorobenzoyl)-(L)-4-(2',6'-bis-methoxyphenyl)phenylalanine (TR14035), 3-(adamantane-1-carbonylamino)-3-(4-ethoxyphenyl) propanoic acid (compound D) or 3-(adamantane-1-carbonylamino)-3-(4-propoxyphenyl) propanoic acid (compound E) and said competitive ligand of said LFA-1 integrin molecule is (2-[2-Chloro-4-(3-hydroxy-benzylcarbamoyl)-benzoylamino]-succinamic acid) (compound 3 of FIG. 9) or (2-[2,6-Dichloro-4-(3-hydroxy-benzylcarbamoyl)-benzoylamino]-3-(3,5-dihydroxy-benzoylamino)-propionic acid) (XVA143), wherein said integrin molecule is expressed on a cell.

2. The method according to claim 1 wherein the decrease in binding of antibody to said integrin molecule is compared to a control wherein the control is a measurement of the non-specific binding of the antibody to the integrin molecule.

3. The method according to claim 1 wherein said integrin molecule is expressed on a wild type cell.

4. The method according to claim 1 wherein said integrin molecule is expressed on an engineered cell.

5. The method according to claim 4 wherein said cell expresses both VLA-4 and LFA-1.

6. The method according to claim 1 wherein said integrin molecule is expressed on a cell selected from the group consisting of human peripheral blood granulocytes, monocytes, lymphocytes and human platelet cells.

7. The method according to claim 2 wherein said integrin molecule is expressed on a cell selected from the group consisting of human peripheral blood granulocytes, monocytes, lymphocytes and human platelet cells.

8. The method according to claim 1 wherein said integrin is expressed on a cell selected from the group consisting of U937 cells, MOLT-4 cells, Jurkat cells, THP-1 cells, HL-60 cells, JY cells and MEG-01 cells.

9. The method according to claim 2 wherein said integrin is expressed on a cell selected from the group consisting of U937 cells, MOLT-4 cells, Jurkat cells, THP-1 cells, HL-60 cells, JY cells and MEG-01 cells.

10. The method according to claim 1 wherein said integrin molecule is VLA-4.

11. The method according to claim 2 wherein said integrin molecule is VLA-4.

12. The method according to claim 4 wherein said integrin molecule is VLA-4.

13. The method according to claim 1 wherein said integrin molecule is LFA-1.

14. The method according to claim 2 wherein said integrin molecule is LFA-1.

15. The method according to claim 4 wherein said integrin molecule is LFA-1.

16. The method according to claim 10 wherein said antibody is monoclonal antibody clone HUTS-21.

17. The method according to claim 11 wherein said antibody is monoclonal antibody clone HUTS-21.

18. The method according to claim 12 wherein said antibody is monoclonal antibody clone HUTS-21.

19. The method according to claim 13 wherein said antibody is monoclonal antibody clone MEM-148.

20. The method according to claim 14 wherein said antibody is monoclonal antibody clone MEM-148.

21. The method according to claim 15 wherein said antibody is monoclonal antibody clone MEM-148.

22. The method according to claim 16 wherein said ligand is, a compound according to the chemical structure:

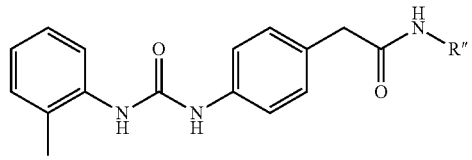

where R" is a peptide LDV or SEQ ID NO:1 (compound LDV) or SEQ ID NO:2 (compound YLDV), the compound TR14035, compound D or compound E.

23. The method according to claim 17 wherein said ligand is, a compound according to the chemical structure:

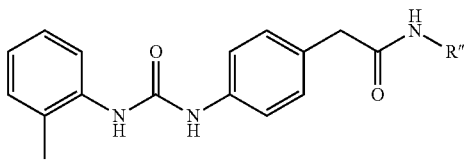

where R" is a peptide of SEQ ID NO:1 (compound LDV) or SEQ ID NO:2 (compound YLDV), the compound TR14035, compound D or compound E.

24. The method according to claim 18 wherein said ligand is, a compound according to the chemical structure:

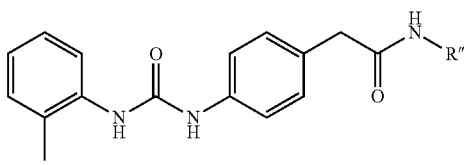

where R" is a peptide of SEQ ID NO:1 (for compound LDV) or SEQ ID NO:2 (for compound YLDV), the compound TR14035, compound D or compound E.

25. The method according to claim 19 wherein said ligand is compound 3 or XVA143.

26. The method according to claim 20 wherein said ligand is compound 3 or XVA143.

27. The method according to claim 21 wherein said ligand is compound 3 or XVA143.

28. The method according to claim 16 wherein said reporter moiety is a fluorophore.

29. The method according to claim 19 wherein said reporter moiety is a fluorophore.

30. The method according to claim 19 wherein said reporter moiety is a fluorophore.

31. The method according to claim 20 wherein said reporter moiety is a fluorophore.

32. The method according to claim 28 wherein said flourophore is selected from the group consisting of fluorescein, isothiocyanate, rhodamine, phycoerythrin, phycocyanin, allophycocyanin, ophthaldehyde label, fluorescamine, tetramethylrhodamine, a dipyrrometheneboron difluoride dye, a near infrared dye and a lanthanide chelate.

33. The method according to claim 29 wherein said flourophore is selected from the group consisting of fluorescein, isothiocyanate, rhodamine, phycoerythrin, phycocyanin, allophycocyanin, ophthaldehyde label, fluorescamine, tetramethylrhodamine, a dipyrrometheneboron difluoride dye, a near infrared dye and a lanthanide chelate.

34. The method according to claim 30 wherein said flourophore is selected from the group consisting of fluorescein, isothiocyanate, rhodamine, phycoerythrin, phycocyanin, allophycocyanin, ophthaldehyde label, fluorescamine, tetramethylrhodamine, a dipyrrometheneboron difluoride dye, a near infrared dye and a lanthanide chelate.

35. The method according to claim 31 wherein said flourophore is selected from the group consisting of fluorescein, isothiocyanate, rhodamine, phycoerythrin, phycocyanin, allophycocyanin, ophthaldehyde label, fluorescamine, tetramethylrhodamine, a dipyrrometheneboron difluoride dye, a near infrared dye and a lanthanide chelate.

36. The method according to claim 28 wherein said fluorophore is fluorescein or phycoerythrin.

37. The method according to claim 30 wherein said fluorophore is fluorescein or phycoerythrin.

38. The method according to claim 1 adapted for use in high throughput flow cytometry.

39. The method according to claim 2 adapted for use in high throughput flow cytometry.

40. The method according to claim 16 adapted for use in high throughput flow cytometry.

41. The method according to claim 19 adapted for use in high throughput flow cytometry.

* * * * *

SEQUENCE LISTING

```
<160> NUMBER OF SEQ ID NOS: 2

<210> SEQ ID NO 1
<211> LENGTH: 7
<212> TYPE: PRT
<213> ORGANISM: Artificial Sequence
<220> FEATURE:
<223> OTHER INFORMATION: LDV Peptide
<220> FEATURE:
<221> NAME/KEY: misc_feature
<222> LOCATION: (7)
<223> OTHER INFORMATION: Xaa is Hyl

<400> SEQUENCE: 1

Leu Asp Val Pro Ala Ala Xaa
1               5

<210> SEQ ID NO 2
<211> LENGTH: 8
<212> TYPE: PRT
<213> ORGANISM: Artificial Sequence
```

```
<220> FEATURE:
<223> OTHER INFORMATION: YLDV Peptide
<220> FEATURE:
<221> NAME/KEY: misc_feature
<222> LOCATION: (8)
<223> OTHER INFORMATION: Xaa is Hyl

<400> SEQUENCE: 2

Tyr Leu Asp Val Pro Ala Ala Xaa
1               5
```